United States Patent
Lechner et al.

(10) Patent No.: US 11,992,546 B2
(45) Date of Patent: *May 28, 2024

(54) PROCESS OF COLORING KERATINOUS MATERIAL COMPRISING THE USE OF AN ORGANOSILICON COMPOUND, AN EFFECT PIGMENT, AND A SEALING REAGENT VI

(71) Applicant: Henkel AG & Co. KGaA, Duesseldorf (DE)

(72) Inventors: Torsten Lechner, Langenfeld (DE); Gabriele Weser, Neuss (DE); Claudia Kolonko, Remscheid (DE); Caroline Kriener, Duesseldorf (DE); Ulrike Schumacher, Duesseldorf (DE); Marc Nowottny, Moenchengladbach (DE); Juergen Schoepgens, Schwalmtal (DE); Phillip Jaiser, Langenfeld (DE); Carsten Mathiaszyk, Essen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/441,265

(22) PCT Filed: Mar. 13, 2020

(86) PCT No.: PCT/EP2020/056814
§ 371 (c)(1),
(2) Date: Sep. 20, 2021

(87) PCT Pub. No.: WO2020/187735
PCT Pub. Date: Sep. 24, 2020

(65) Prior Publication Data
US 2022/0151904 A1 May 19, 2022

(30) Foreign Application Priority Data
Mar. 19, 2019 (DE) .................... 102019203668

(51) Int. Cl.
| *A61Q 5/10* | (2006.01) |
| *A61K 8/26* | (2006.01) |
| *A61K 8/58* | (2006.01) |
| *A61K 8/73* | (2006.01) |
| *A61K 8/81* | (2006.01) |
| *A61K 8/891* | (2006.01) |
| *A61Q 5/06* | (2006.01) |

(52) U.S. Cl.
CPC ............. *A61K 8/585* (2013.01); *A61K 8/26* (2013.01); *A61K 8/731* (2013.01); *A61K 8/8152* (2013.01); *A61K 8/891* (2013.01); *A61Q 5/06* (2013.01); *A61K 2800/884* (2013.01)

(58) Field of Classification Search
CPC .......... A61K 8/585; A61K 8/26; A61K 8/731; A61K 8/8152; A61K 8/891; A61K 2800/884; A61K 2800/54; A61K 2800/95; A61K 8/8147; A61K 2800/412; A61K 2800/5922; A61K 2800/623; A61K 2800/94; A61K 8/0262; A61Q 5/06
USPC ............................................. 8/405
See application file for complete search history.

(56) References Cited

U.S. PATENT DOCUMENTS

| 2001/0007160 A1* | 7/2001 | Yamaguchi ........... A61Q 5/10 8/405 |
| 2010/0083446 A1 | 4/2010 | Brun et al. |
| 2010/0083466 A1* | 4/2010 | Andersen ............. B65G 17/08 16/266 |
| 2010/0303748 A1* | 12/2010 | Hercouet .............. A61Q 5/10 8/405 |
| 2015/0313814 A1 | 11/2015 | Lawson et al. |

FOREIGN PATENT DOCUMENTS

| EP | 2168633 A2 | 3/2010 |
| EP | 3081601 A1 | 10/2016 |
| WO | 2005075578 A2 | 8/2005 |
| WO | 2013068979 A2 | 5/2013 |
| WO | 2018130912 A1 | 7/2018 |

* cited by examiner

Primary Examiner — Eisa B Elhilo
(74) Attorney, Agent, or Firm — Lorenz & Kopf, LLP

(57) ABSTRACT

Provided herein is a process for dyeing keratinous material, in particular human hair, comprising the following steps:
  Application of an agent (a) to the keratinous material, wherein the agent (a) comprises:
    (a1) at least one organic silicon compound selected from the group of silanes having one, two or three silicon atoms, and
    (a2) at least one colorant compound comprising at least one substrate platelet-based pigment comprising a vacuum metallized pigment, and
  Application of an agent (b) to the keratinous material, wherein the agent (b) comprises:
    (b1) at least one sealing reagent.

20 Claims, No Drawings

PROCESS OF COLORING KERATINOUS MATERIAL COMPRISING THE USE OF AN ORGANOSILICON COMPOUND, AN EFFECT PIGMENT, AND A SEALING REAGENT VI

CROSS-REFERENCE TO RELATED APPLICATION

This application is a U.S. National-Stage entry under 35 U.S.C. § 371 based on International Application No. PCT/EP2020/056814, filed Mar. 13, 2020, which was published under PCT Article 21(2) and which claims priority to German Application No. 102019203668.6, filed Mar. 19, 2019, which are all hereby incorporated in their entirety by reference.

TECHNICAL FIELD

The subject of the present application is a method for treating keratinous material, in particular human hair, which comprises the application of two agents (a) and (b). The agent (a) is exemplified by its content of at least one organic silicon compound (a1) and at least one selected coloring compound (a2). The agent (b) contains at least one sealing reagent.

A further subject of this application is a multi-component packaging unit (kit-of-parts) for dyeing keratinous material, in particular human hair, which comprises separately prepared at least four agents (a'), (a") and (b). Agents (a') and (a") can be used to prepare the agent (a) used in the process described above.

BACKGROUND

The change in shape and color of keratin fibers, especially hair, is an important area of modern cosmetics. To change the hair color, the expert knows various coloring systems depending on coloring requirements. Oxidation dyes are usually used for permanent, intensive dyeings with good fastness properties and good grey coverage. Such dyes usually contain oxidation dye precursors, so-called developer components and coupler components, which form the actual dyes with one another under the influence of oxidizing agents, such as hydrogen peroxide. Oxidation have very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed without residue by a few washes with surfactant-containing cleaning agents. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. The paper teaches that when the combination of a pigment, an organic silicon compound, a film-forming polymer and a solvent is used on hair, it is possible to create colorations that are particularly resistant to shampooing.

Metallic luster pigments or metallic effect pigments are widely used in many fields of technology. They are used, for example, to color coatings, printing inks, inks, plastics, glasses, ceramic products, and preparations for decorative cosmetics such as nail polish. They have attractive angle-dependent color impression (goniochromism) and metallic-looking luster.

Hair with a metallic finish or metallic highlights are in trend. The metallic tone makes the hair look thicker and shinier.

There is a need to provide hair dyes with effect pigments that on the one hand have high wash and rub fastness and on the other hand do not negatively affect hair properties such as manageability and feel. For this purpose, it would be desirable if the effect pigments used had a high covering power and could be applied to the hair in thin layers.

Accordingly, the task of the present disclosure was to provide a coloring system with effect pigments that has fastness properties comparable to oxidative coloring. Wash fastness properties should be outstanding, but the use of oxidation dye precursors normally used for this purpose should be avoided.

BRIEF SUMMARY

Processes for dyeing keratinous material and kits-of-parts are provided herein. In an embodiment, a process for dyeing keratinous material includes applying an agent (a) to the keratinous material, wherein the agent (a) includes (a1) at least one organic silicon compound selected from the group of silanes having one, two or three silicon atoms, and (a2) at least one colorant compound comprising at least one substrate platelet-based pigment comprising a vacuum metallized pigment. An agent (b) is applied to the keratinous material, wherein the agent (b) includes: (b1) at least one sealing reagent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been found that the task can be excellently solved if keratinous materials, in particular human hair, are colored by a process in which at least two agents (a) and (b) are applied to the keratinous materials (hair). Here, the first agent (a) contains at least one organic silicon compound from the group of silanes with one, two or three silicon atoms, and further at least one selected coloring compound. In the medium (a), the organic silicon compound and the colorant compound are thus prepared together. The second agent (b) contains at least one sealing reagent.

When the two agents (a) and (b) were used in a dyeing process, keratinous material could be dyed with particularly high color intensity.

A first object as contemplated herein is a method for coloring keratinous material, in particular human hair, comprising the following steps:

Application of an agent (a) to the keratinous material, wherein the agent (a) comprises:
(a1) at least one organic silicon compound selected from the group of silanes having one, two or three silicon atoms, and
(a2) at least one colorant compound comprising at least one substrate platelet-based pigment comprising a vacuum metallized pigment, and
Application of an agent (b) to the keratinous material, wherein the agent (b) comprises:
(b1) at least one sealing reagent.

In the work leading to the present disclosure, it has been found that the preferential successive application of agents (a) and (b) enables the production of very stable and washfast colorations on the keratinous materials. Without being limited to this theory, it is suspected in this context that the joint application of organic silicon compound (a1) and color-imparting compound (a2) leads to the formation of a particularly resistant first film on the keratinous material. The first layer is sealed with the application of the second agent (b). For example, a film-forming polymer is now deposited on this first layer as a sealing reagent (b1) in the form of a further film.

Due to this special type of packaging—i.e. the joint application of silane (a1) and color-imparting compound (a2) and separate application of the sealing reagent (b1)—the film system produced in this way exhibited improved resistance to external influences. In this way, the colorant compounds (a2) were permanently fixed to the keratinous material, so that extremely washfast colorations with good resistance to shampooing could be obtained.

Keratinous Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

Agent (a) and (b)

In the process as contemplated herein, agents (a) and (b) are applied to the keratinous material, in particular human hair. The two agents (a) and (b) are different from each other.

In other words, a first object as contemplated herein is a method for treating keratinous material, in particular human hair, comprising the following steps:

Application of an agent (a) to the keratinous material, wherein the agent (a) comprises:
(a1) at least one organic silicon compound selected from the group of silanes having one, two or three silicon atoms, and
(a2) at least one colorant compound comprising at least one substrate platelet-based pigment comprising a vacuum metallized pigment, and Application of an agent (b) to the keratinous material, wherein the agent (b) comprises:
(b1) at least one sealing reagent.

Agent (a)

Preferably, the composition (a) contains the ingredients (a1) and (a2) in a cosmetic carrier, particularly preferably in an aqueous or aqueous-alcoholic cosmetic carrier. This cosmetic carrier can be liquid, gel, or cream. Pasty, solid or powdery cosmetic carriers can also be used for the preparation of agent (a). For hair treatment, in particular hair coloring, such carriers are, for example, creams, emulsions, gels, or also surfactant-containing foaming solutions, such as shampoos, foam aerosols, foam formulations or other preparations suitable for application to the hair.

Preferably, the cosmetic carrier contains—based on its weight—at least about 2% by weight of water. Further preferably, the water content is above about 10% by weight, still further preferably above about 20% by weight and particularly preferably above about 40% by weight. The cosmetic carrier can also be aqueous alcoholic. Aqueous/alcoholic solutions as contemplated herein are aqueous solutions containing from about 2 to about 70% by weight of a C1-C4 alcohol, more particularly ethanol or isopropanol. The agents as contemplated herein may additionally contain other organic solvents, such as methoxy butanol, benzyl alcohol, ethyl diglycol or 1,2-propylene glycol. Preferred are all water-soluble organic solvents.

Organic Silicon Compounds from the Group of Silanes (a1)

As an ingredient (a1), the composition (a) contains at least one organic silicon compound from the group of silanes having one, two or three silicon atoms.

Particularly preferably, the agent (a) contains at least one organic silicon compound (a1) selected from silanes having one, two or three silicon atoms, the organic silicon compound comprising one or more hydroxyl groups and/or hydrolysable groups per molecule.

These organic silicon compounds (a1) or organic silanes contained in the agent (a) is reactive compounds.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds as contemplated herein are compounds containing one to three silicon atoms. Organic silicon compounds preferably contain one or two silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

In a particularly preferred embodiment, a method as contemplated herein includes applying an agent (a) to the keratinous material, said agent (a) comprising at least one organic silicon compound (a1) selected from silanes having one, two or three silicon atoms, said organic silicon compound further comprising one or more hydroxyl groups or hydrolysable groups per molecule.

In a very particularly preferred embodiment, a process as contemplated herein includes applying an agent (a) to the keratinous material, said agent (a) comprising at least one organic silicon compound (a1) selected from silanes having one, two or three silicon atoms, said organic silicon compound further comprising one or more basic chemical functions and one or more hydroxyl groups or hydrolysable groups per molecule.

This basic group or basic chemical function can be, for example, an amino group, an alkylamino group or a dialkylamino group, which is preferably connected to a silicon atom via a linker. Preferably, the basic group is an amino group, a C1-C6 alkylamino group or a di(C1-C6)alkylamino group.

The hydrolysable group(s) is (are) preferably a C1-C6 alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R"R'"Si—O—CH2-

CH3. The residues R', R" and R'" represent the three remaining free valences of the silicon atom.

A particularly preferred method as contemplated herein is exemplified in that the composition comprises (a) at least one organic silicon compound selected from silanes having one, two or three silicon atoms, the organic silicon compound preferably comprising one or more basic chemical functions and one or more hydroxyl groups or hydrolysable groups per molecule.

Particularly good results were obtained when the agent (a) contains at least one organic silicon (a1) compound of formula (I) and/or (II).

The compounds of formulas (I) and (II) are organic silicon compounds selected from silanes having one, two or three silicon atoms, the organic silicon compound comprising one or more hydroxyl groups and/or hydrolysable groups per molecule.

In another very particularly preferred embodiment, the agent is applied to the keratinous material (or human hair), the agent (a) comprising at least one organic silicon compound (a) of formula (I) and/or (II), R1R2N-L-Si(OR3)a(R4)b     (I), where
R1, R2 independently represent a hydrogen atom or a C1-C6 alkyl group,
L is a linear or branched divalent C1-C20 alkylene group,
R3 is a hydrogen atom or a C1-C6 alkyl group,
R4 represents a C1-C6 alkyl group
a, stands for an integer from 1 to 3, and
b stands for the integer 3−a, (R5O)c(R6)dSi-(A)e-[NR7-(A')]f-[O-(A")]g-[NR8-(A'")]h-Si(R6')d'(OR5')c'     (II), where
R5, R5', R5" independently represent a hydrogen atom or a C1-C6 alkyl group,
R6, R6' and R6" independently represent a C1-C6 alkyl group,
A, A', A", independently of one another represent a linear or branched divalent C1-C20 alkylene group
R7 and R8 independently represent a hydrogen atom, a C1-C6 alkyl group, a hydroxy C1-C6 alkyl group, a C2-C6 alkenyl group, an amino C1-C6 alkyl group or a group of formula (III)

(A"")-Si(R6")d"(OR5")c"     (III), c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g, and h is different from 0.

The substituents R1, R2, R3, R4, R5, R5', R5", R6, R6', R6", R7, R8, L, A', A"" and A"" in the compounds of formula (I) and (II) are explained below as examples:

Examples of a C1-C6 alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a C2-C6 alkenyl group are vinyl, allyl, but-2-enyl, but-3-enyl and isobutenyl, preferred C2-C6 alkenyl radicals are vinyl and allyl. Preferred examples of a hydroxy C1-C6 alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino C1-C6 alkyl group are the aminomethyl, the 2-aminoethyl group, the 3-aminopropyl group. The 2-aminoethyl group is particularly preferred. Examples of a linear divalent C1-C20 alkylene group include the methylene group (—CH2), the ethylene group (—CH2-CH2-), the propylene group (—CH2-CH2-CH2-) and the butylene group (—CH2-CH2-CH2-). The propylene group (—CH2-CH2-CH2-) is particularly preferred. From a chain length of 3 C atoms, divalent alkylene groups can also be branched. Examples of branched divalent C3-C20 alkylene groups are (—CH2-CH(CH3)-) and (—CH2-CH(CH3)-CH2-).

In the organic silicon compounds of the formula (I)

R1R2N-L-Si(OR3)a(R4)b     (I), the radicals R1 and R2 independently of one another represent a hydrogen atom or a C1-C6 alkyl group. In particular, the radicals R1 and R2 both represent a hydrogen atom.

In the middle part of the organic silicon compound is the structural unit or the linker -L- which stands for a linear or branched, divalent C1-C20 alkylene group.

A divalent C1-C20 alkylene group may alternatively be referred to as a divalent or divalent C1-C20 alkylene group, by which is meant that each L grouping may form two bonds. One bond is from the amino group R1R2N to the linker L, and the second bond is between the linker L and the silicon atom.

Preferably, -L- represents a linear, divalent (i.e., divalent) C1-C20 alkylene group. Further preferably -L- stands for a linear divalent C1-C6 alkylene group. Particularly preferred -L stands for a methylene group (CH2-), an ethylene group (—CH2-CH2-), propylene group (—CH2-CH2-CH2-) or butylene (—CH2-CH2-CH2-CH2-). L stands for a propylene group (—CH2-CH2-CH2-) The linear propylene group (—CH2-CH2-CH2-) can alternatively be referred to as the propane-1,3-diyl group.

The organic silicon compounds of formula (I)

R1R2N-L-Si(OR3)a(R4)b(I), one end of each carries the silicon-containing group
—Si(OR3)a(R4)b In the terminal structural unit —Si(OR3)a(R4)b, R3 is hydrogen or C1-C6 alkyl group, and R4 is C1-C6 alkyl group. Particularly preferred, R3 and R4 independently of each other represent a methyl group or an ethyl group.

Here a stands for an integer from 1 to 3, and b stands for the integer 3−a. If a stands for the number 3, then b is equal to 0. If a stands for the number 2, then b is equal to 1. If a stands for the number 1, then b is equal to 2.

Particularly resistant films could be produced if the agent (a) contains at least one organic silicon compound (a1) of formula (I) in which the radicals R3, R4 independently of one another represent a methyl group or an ethyl group.

When using the process as contemplated herein for dyeing keratinous material, dyeings with the best wash fastnesses could be obtained analogously when the agent (a) contains at least one organic silicon compound of formula (I) in which the radicals R3, R4 independently of one another represent a methyl group or an ethyl group.

Furthermore, dyeings with the best wash fastnesses could be obtained if the agent (a) contains at least one organic silicon compound of the formula (I) in which the radical a represents the number 3. In this case the rest b stands for the number 0.

In a further preferred embodiment, the agent (a) used comprises at least one organic silicon compound (a1) of formula (I), wherein R3, R4 independently of one another represent a methyl group or an ethyl group and
a stands for the number 3 and
b stands for the number 0.

In a further preferred embodiment, the agent (a) comprises at least one organic silicon compound (a1) of the formula (I), R1R2N-L-Si(OR3)a(R4)b      (I), where
R1, R2 both represent a hydrogen atom, and
L represents a linear, divalent C1-C6-alkylene group, preferably a propylene group (—CH2-CH2-CH2-) or an ethylene group (—CH2-CH2-),
R3 represents a hydrogen atom, an ethyl group, or a methyl group,
R4 represents a methyl group or an ethyl group,
a stands for the number 3 and
b stands for the number 0.

Organic silicon compounds of the formula (I) which are particularly suitable are
(3-Aminopropyl)triethoxysilane

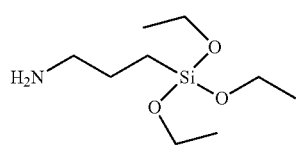

(3-Aminopropyl)trimethoxysilane

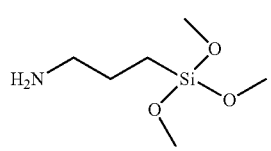

1-(3-Aminopropyl)silantriol

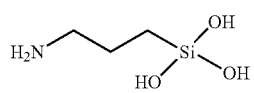

(2-Aminoethyl)triethoxysilane

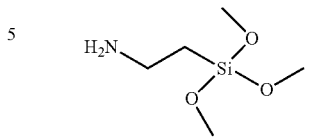

(2-Aminoethyl)trimethoxysilane

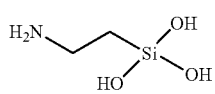

1-(2-Aminoethyl)silantriol

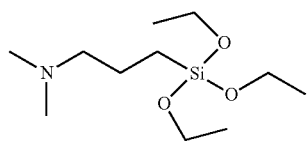 [SMILES: CCO[Si](CCCN(C)C)(OCC)OCC]

(3-Dimethylaminopropyl)triethoxysilane

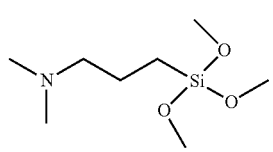

(3-Dimethylaminopropyl)trimethoxysilane

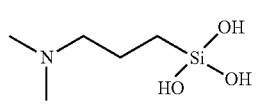

1-(3-Dimethylaminopropyl)silantriol

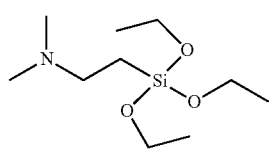

(2-Dimethylaminoethyl)triethoxysilane

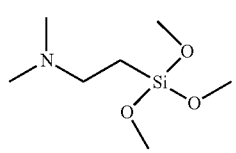

(2-dimethylaminoethyl)trimethoxysilane and 1-(2-Dimethylaminoethyl)silantriol

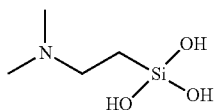

In a further preferred embodiment, the agent (a) comprises at least one organic silicon compound (a1) selected from the group of
(3-Aminopropyl)triethoxysilan
(3-Aminopropyl)trimethoxysilane
1-(3-Aminopropyl)silantriol
(2-Aminoethyl)triethoxysilane
(2-Aminoethyl)trimethoxysilane
1-(2-Aminoethyl)silantriol
(3-Dimethylaminopropyl)triethoxysilane
(3-Dimethylaminopropyl)trimethoxysilane
1-(3-Dimethylaminopropyl)silantriol
(2-Dimethylaminoethyl)triethoxysilane.
(2-Dimethylaminoethyl)trimethoxysilane and/or
1-(2-Dimethylaminoethyl)silantriol.

The organic silicon compounds of formula (I) are commercially available. (3-aminopropyl)trimethoxysilane, for example, can be purchased from Sigma-Aldrich. Also (3-aminopropyl)triethoxysilane is commercially available from Sigma-Aldrich.

In a further embodiment, the composition as contemplated herein comprises at least one organic silicon compound (a1) of the formula (II)

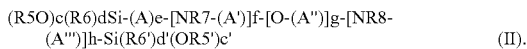
(II).

The organosilicon compounds of formula (II) as contemplated herein each carry the silicon-containing groups (R5O)c(R6)dSi- and —Si(R6')d'(OR5')c at both ends.

In the central part of the molecule of formula (II) there are the groups -(A)e- and —[NR7-(A')]f- and —[O-(A")]g- and —[NR8-(A'")]h-. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group of -(A)- and —[NR7-(A')]- and —[O-(A")]- and —[NR8-(A'")]-.

In the two terminal structural units (R5O)c(R6)dSii- and —Si(R6')d'(OR5')c, the radicals R5, R5', R5" independently of one another represent a hydrogen atom or a C1-C6 alkyl group. The radicals R6, R6' and R6" independently represent a C1-C6 alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Films with the highest stability or dyes with the best wash fastnesses could be obtained when the residues c and c' both stand for the number 3. In this case d and d' both stand for the number 0.

In another preferred embodiment, the agent (a) comprises at least one organic silicon compound (a1) of formula (II),

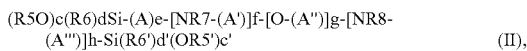
(II), where
R5 and R5' independently represent a methyl group or an ethyl group,
c and c' both stand for the number 3 and
d and d' both stand for the number 0.

If c and c' are both the number 3 and d and d' are both the number 0, the organic silicon compound as contemplated herein corresponds to formula (IIa)

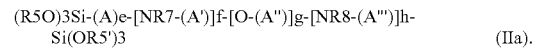
(IIa).

The radicals e, f, g, and h can independently stand for the number 0 or 1, whereby at least one radical from e, f, g, and h is different from zero. The abbreviations e, f, g, and h thus define which of the groupings -(A)e- and —[NR7-(A')]f- and —[O-(A")]g- and —[NR8-(A'")]h- are in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

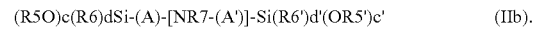
(IIb).

The radicals A, A', A", A'" and A"" independently represent a linear or branched divalent C1-C20 alkylene group. Preferably the radicals A, A', A", A'" and A"" independently of one another represent a linear, divalent C1-C20 alkylene group. Further preferably the radicals A, A', A", A'" and A"" independently represent a linear divalent C1-C6 alkylene group. In particular, the radicals A, A', A", A'" and A"" independently of one another represent a methylene group (—CH2-), an ethylene group (—CH2-CH2-), a propylene group (—CH2-CH2-CH2-) or a butylene group (—CH2-CH2-CH2-CH2-). In particular, the radicals A, A', A", A'" and A'" stand for a propylene group (—CH2-CH2-CH2-).

The divalent C1-C20 alkylene group may alternatively be referred to as a divalent or divalent C1-C20 alkylene group, by which is meant that each grouping A, A', A", A'" and A'" may form two bonds.

The linear propylene group (—CH2-CH2-CH2-) can alternatively be referred to as the propane-1,3-diyl group.

If the radical f represents the number 1, then the organic silicon compound of formula (II) as contemplated herein contains a structural grouping —[NR7-(A')]-.

If the radical f represents the number 1, then the organic silicon compound of formula (II) as contemplated herein contains a structural grouping —[NR8-(A'")]-.

Wherein R7 and R7 independently represent a hydrogen atom, a C1-C6 alkyl group, a hydroxy-C1-C6 alkyl group, a C2-C6 alkenyl group, an amino-C1-C6 alkyl group or a group of the formula (III)

(III).

Very preferably the radicals R7 and R8 independently of one another represent a hydrogen atom, a methyl group, a 2-hydroxyethyl group, a 2-alkenyl group, a 2-aminoethyl group or a grouping of the formula (III).

When the radical f represents the number 1 and the radical h represents the number 0, the organic silicon compound as contemplated herein contains the grouping [NR7-(A')] but not the grouping —[NR8-(A")]. If the radical R7 now stands for a grouping of the formula (III), the agent (a) contains an organic silicon compound with 3 reactive silane groups.

In another preferred embodiment, the agent (a) comprises at least one organic silicon compound (a1) of formula (II),

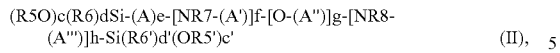

where
- e and f both stand for the number 1,
- g and h both stand for the number 0,
- A and A' independently represent a linear, divalent C1-C6 alkylene group and
- R7 represents a hydrogen atom, a methyl group, a 2-hydroxyethyl group, a 2-alkenyl group, a 2-aminoethyl group or a group of formula (III).

In a further preferred embodiment, the agent (a) comprises at least one organic silicon compound of formula (II), wherein
- e and f both stand for the number 1,
- g and h both stand for the number 0,
- A and A' independently of one another represent a methylene group (—CH2-), an ethylene group (—CH2-CH2-) or a propylene group (—CH2-CH2-CH2), and
- R7 represents a hydrogen atom, a methyl group, a 2-hydroxyethyl group, a 2-alkenyl group, a 2-aminoethyl group or a group of formula (III).

Organic silicon compounds of formula (II) which are well suited for solving the problem as contemplated herein are:

3-(Trimethoxysilyl)-N-[3-(trimethoxysilyl)propyl]-1-propanamine

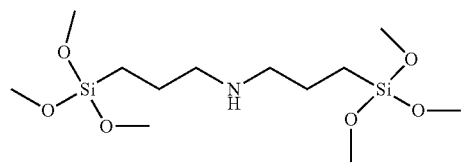

3-(Triethoxysilyl)-N-[3-(triethoxysilyl) propyl]-1-propanamine

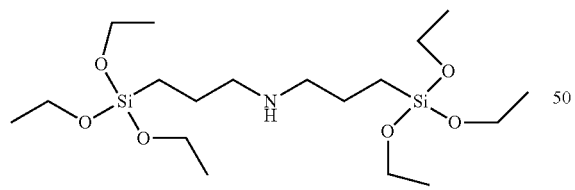

N-methyl-3-(trimethoxysilyl)-N-[3-(trimethoxysilyl) propyl]-1-propanamine

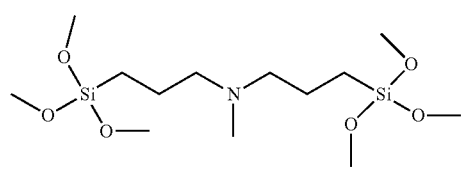

N-Methyl-3-(triethoxysilyl)-N-[3-(triethoxysilyl) propyl]-1-propanamine

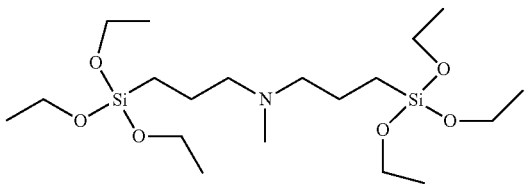 [SMILES: CCO[Si](CCCN(C)CCC[Si](OCC)(OCC)OCC)(OCC)OCC]

2-[Bis[3-(trimethoxysilyl) propyl]amino]-ethanol

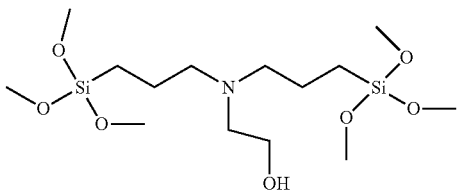

2-[bis[3-(triethoxysilyl) propyl]amino]ethanol

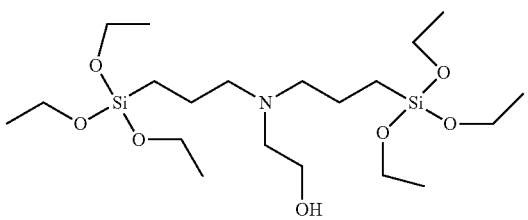 [SMILES: CCO[Si](CCCN(CCO)CCC[Si](OCC)(OCC)OCC)(OCC)OCC]

3-(Trimethoxysilyl)-N,N-bis[3-(trimethoxysilyl)propyl]-1-propanamine

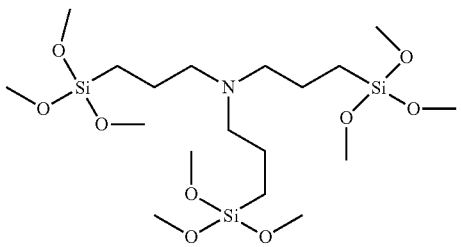

3-(Triethoxysilyl)-N,N-bis[3-(triethoxysilyl)propyl]-1-propanamine

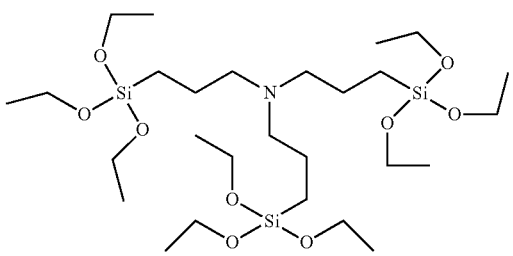 [SMILES: CCO[Si](CCCN(CCC[Si](OCC)(OCC)OCC)CCC[Si](OCC)(OCC)OCC)(OCC)OCC]

N1,N1-Bis[3-(trimethoxysilyl)propyl]-1,2-ethanediamine,

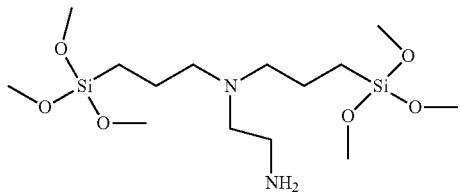

N1,N1-Bis[3-(triethoxysilyl)propyl]-1,2-ethanediamine,

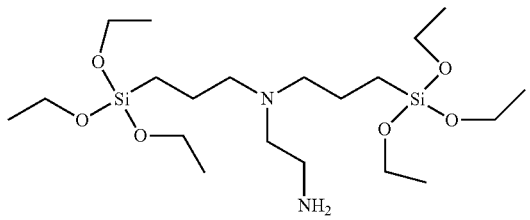 [SMILES: CCO[Si](CCCN(CCN)CCC[Si](OCC)(OCC)OCC)(OCC)OCC]

N,N-Bis[3-(trimethoxysilyl)propyl]-2-propene-1-amine

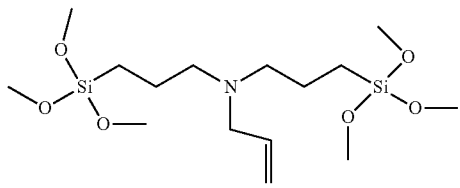

N,N-Bis[3-(triethoxysilyl)propyl]-2-propene-1-amine

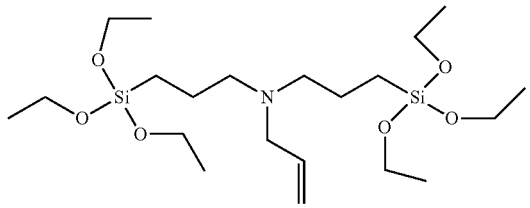 [SMILES: C=CCN(CCC[Si](OCC)(OCC)OCC)CCC[Si](OCC)(OCC)OCC]

The organic silicon compounds of formula (II) are commercially available. Bis(trimethoxysilylpropyl)amines with the CAS number 82985-35-1 can be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased for example from Fluorochem or Sigma-Aldrich.

In a further preferred embodiment, the agent (a) comprises at least one organic silicon compound (a1) selected from the group of 3-(Trimethoxysilyl)-N-[3-(trimethoxysilyl)propyl]-1-propanamine
3-(Triethoxysilyl)-N-[3-(triethoxysilyl) propyl]-1-propanamine
N-methyl-3-(trimethoxysilyl)-N-[3-(trimethoxysilyl) propyl]-1-propanamine
N-Methyl-3-(triethoxysilyl)-N-[3-(triethoxysilyl) propyl]-1-propanamine
2-[Bis[3-(trimethoxysilyl) propyl]amino]-ethanol
2-[bis[3-(triethoxysilyl) propyl]amino]ethanol
3-(Trimethoxysilyl)-N,N-bis[3-(trimethoxysilyl) propyl]-1-propanamine
3-(Triethoxysilyl)-N,N-bis[3-(triethoxysilyl) propyl]-1-propanamine
N1,N1-bis[3-(trimethoxysilyl) propyl]-1,2-ethanediamine,
N1,N1-bis[3-(triethoxysilyl) propyl]-1,2-ethanediamine,
N,N-bis[3-(trimethoxysilyl)propyl]-2-propen-1-amine and/or
N,N-bis[3-(triethoxysilyl)propyl]-2-propen-1-amine.

In further tests, in particular dyeing tests, it has also been found to be particularly advantageous if the agent (a) applied to the keratinous material in the process contains at least one organic silicon compound of the formula (IV)

$$R9Si(OR10)k(R11)m \qquad (IV).$$

The compounds of formula (IV) are organic silicon compounds selected from silanes having one, two or three silicon atoms, the organic silicon compound comprising one or more hydroxyl groups and/or hydrolysable groups per molecule.

The organic silicon compound(s) of formula (IV) may also be called a silane of the alkyl-alkoxy-silane or alkyl-hydroxy-silane type, $$R9Si(OR10)k(R11)m \qquad (IV),$$

where
R9 stands for a C1-C18 alkyl group,
R10 represents a hydrogen atom or a C1-C6 alkyl group,
R11 represents a C1-C6 alkyl group
k is an integer from 1 to 3, and
m stands for the integer 3–k.

In a further preferred embodiment, the agent (a) comprises at least one organic silicon compound (a1) of formula (IV)

$$R9Si(OR10)k(R11)m \qquad (IV),$$

where
R9 stands for a C1-C18 alkyl group,
R10 represents a hydrogen atom or a C1-C6 alkyl group,
R11 represents a C1-C6 alkyl group
k is an integer from 1 to 3, and
m stands for the integer 3–k.

In a further preferred embodiment, the agent (a) comprises, in addition to the organic silicon compound or compounds of formula (I), at least one further organic silicon compound of formula (IV)

$$R9Si(OR10)k(R11)m \qquad (IV),$$

where
R9 stands for a C1-C18 alkyl group,
R10 represents a hydrogen atom or a C1-C6 alkyl group,
R11 represents a C1-C6 alkyl group
k is an integer from 1 to 3, and
m stands for the integer 3–k.

In a further preferred embodiment, the agent (a) comprises, in addition to the organic silicon compound or compounds of formula (II), at least one further organic silicon compound of formula (IV)

R9Si(OR10)k(R11)m    (IV), where
R9 stands for a C1-C18 alkyl group,
R10 represents a hydrogen atom or a C1-C6 alkyl group,
R11 represents a C1-C6 alkyl group
k is an integer from 1 to 3, and
m stands for the integer 3–k.

In a further preferred embodiment, the agent (a) comprises, in addition to the organic silicon compound or compounds of formula (I) and/or (II), at least one further organic silicon compound of formula (IV)

R9Si(OR10)k(R11)m    (IV), where
R9 stands for a C1-C18 alkyl group,
R10 represents a hydrogen atom or a C1-C6 alkyl group,
R11 represents a C1-C6 alkyl group
k is an integer from 1 to 3, and
m stands for the integer 3–k.

In the organic silicon compounds of formula (IV), the radical R9 represents a C1-C18 alkyl group. This C1-C18 alkyl group is saturated and can be linear or branched. Preferably, R9 represents a linear C1-C18 alkyl group. Preferably, R9 represents a methyl group, an ethyl group, an n-propyl group, an n-butyl group, an n-pentyl group, an n-hexyl group, an n-octyl group, an n-dodecyl group or an n-octadecyl group. Particularly preferably, R9 represents a methyl group, an ethyl group, an n-hexyl group or an n-octyl group.

In the organic silicon compounds of form (IV), the R10 radical represents a hydrogen atom or a C1-C6 alkyl group. Especially preferably, R10 stands for a methyl group or an ethyl group.

In the organic silicon compounds of form (IV), the radical R11 represents a C1-C6 alkyl group. Particularly preferably, R11 represents a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Particularly stable films, i.e., dyeings with particularly good wash fastness properties, could be obtained if an agent (a) containing at least one organic silicon compound (a1) corresponding to formula (IV): in which the radical k is the number 3, was used in the process. In this case the rest m stands for the number 0.

Organic silicon compounds of the formula (IV) which are particularly suitable are
Methyltrimethoxysilane

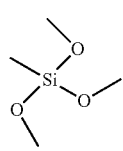

Methyltriethoxysilane

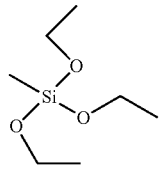

Ethyltrimethoxysilane

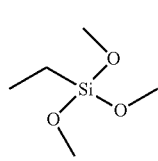

Ethyltriethoxysilane

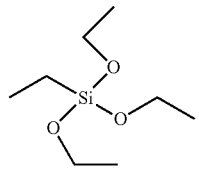

n-Hexyltrimethoxysilane

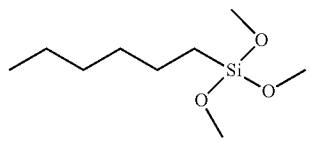

n-Hexyltriethoxysilane

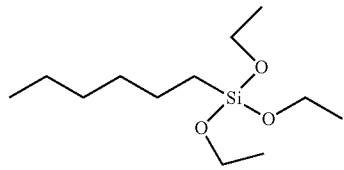 [SMILES: CCCCCC[Si](OCC)(OCC)OCC]

n-Octyltrimethoxysilane

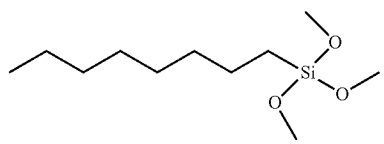

n-Octyltriethoxysilane

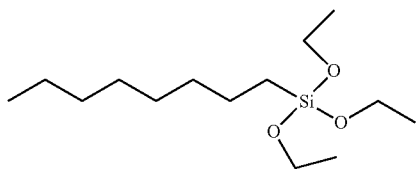 [SMILES: CCCCCCCC[Si](OCC)(OCC)OCC]

n-dodecyltrimethoxysilane and/or

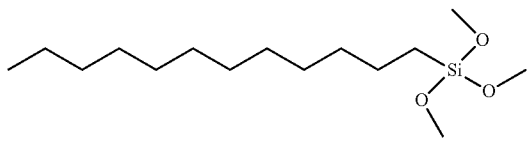 [SMILES: CCCCCCCCCCCC[Si](OC)(OC)OC]

n-dodecyltriethoxysilane.

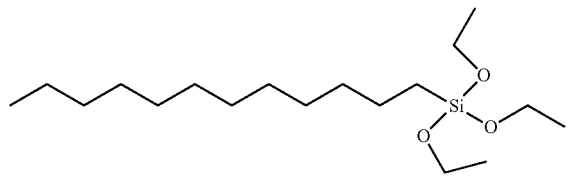 [SMILES: CCCCCCCCCCCC[Si](OCC)(OCC)OCC]

n-octadecyltrimethoxysilane and/or n-octadecyltriethoxysilane.

In a further preferred embodiment, the agent (a) comprises at least one organic silicon compound (a1) of formula (IV) selected from the group of
Methyltrimethoxysilane,
Methyltriethoxysilane,
Ethyltrimethoxysilane,
Ethyltriethoxysilane,
Hexyltrimethoxysilane,
Hexyltriethoxysilane,
Octyltrimethoxysilane,
Octyltriethoxysilane,
Dodecyltrimethoxysilane,
Dodecyltriethoxysilane,
Octadecyltrimethoxysilane, and/or
Octadecyltriethoxysilane.

The organic silicon compounds described above are reactive compounds. In this context, it has been found preferable if the agent (a) contains—based on the total weight of the agent (a)—one or more organic silicon compounds (a1) in a total amount of from about 0.1 to about 20% by weight, preferably from about 1 to about 15% by weight and particularly preferably from about 2 to about 8% by weight.

In a further preferred embodiment, the agent (a) contains—based on the total weight of the agent (a)—one or more organic silicon compounds (a1) in a total amount of from about 0.1 to about 20% by weight, preferably from about 1 to about 15% by weight and particularly preferably from about 2 to about 8% by weight.

To achieve particularly good dyeing results, it is particularly advantageous to use the organic silicon compounds of the formula (I) and/or (II) in certain quantity ranges on average (a). Particularly preferably, the agent (a) contains—based on the total weight of the agent (a)—one or more organic silicon compounds of the formula (I) and/or (II) in a total amount of from about 0.1 to about 10% by weight, preferably from about 0.5 to about 5% by weight and particularly preferably from about 0.5 to about 3% by weight.

In a further preferred embodiment, the agent (a) contains—based on the total weight of the agent (a)—one or more organic silicon compounds of the formula (I) and/or (II) in a total amount of from about 0.1 to about 10% by weight, preferably from about 0.5 to about 5% by weight and particularly preferably from about 0.5 to about 3% by weight.

Furthermore, it has proven to be particularly preferred if the organic silicon compound(s) of formula (IV) is (are) also present in certain quantity ranges in average (a). Particularly preferably, the agent (a) contains—based on the total weight of the agent (a)—one or more organic silicon compounds of the formula (IV) in a total amount of from about 0.1 to about 20% by weight, preferably from about 2 to about 15% by weight and particularly preferably from about 4 to about 9% by weight.

In a further preferred embodiment, the agent (a) contains—based on the total weight of the agent (a)—one or more organic silicon compounds of the formula (IV) in a total amount of from about 0.1 to about 20% by weight, preferably from about 2 to about 15% by weight and particularly preferably from about 3.2 to about 10% by weight.

In the course of the work leading to the present disclosure, it was found that particularly stable and uniform films could be obtained on the keratinous material even when the agent (a) contained two organic silicon compounds that were structurally different from each other.

In another preferred embodiment, the agent (a) contains at least two structurally different organic silicon compounds.

In a preferred embodiment, an agent (a) comprising at least one organic silicone compound of formula (I) and at least one organic silicone compound of formula (IV) is applied to the keratinous material.

In an explicitly quite particularly preferred embodiment, an agent (a) is applied to the keratinous material, which agent contains at least one organic silicon compound of the formula (I) selected from the group of (3-aminopropyl)triethoxysilane and (3-aminopropyl)trimethoxysilane and additionally containing at least one organic silicon compound of formula (IV) selected from the group of methyltrimethoxysilane, methyltriethoxysilane, ethyltrimethoxysilane, ethyltriethoxysilane, hexyltrimethoxysilane and hexyltriethoxysilane.

In a further preferred embodiment, the agent (a) comprises—based on the total weight of the agent (a):
from about 0.5 to about 5% by weight % of at least one first organic silicon compound (a1) which is selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and
from about 3.2 to about 10 wt. % of at least one second organic silicon compound (a1) selected from the group of methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In this embodiment, the agent (a) comprises one or more organic silicon compounds of a first group in a total amount of from about 0.5 to about 3% by weight. The organic silicon compounds of this first group are selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and/or (2-dimethylaminoethyl)triethoxysilane.

In this embodiment, the agent (a) comprises one or more organic silicon compounds of a second group in a total amount of from about 3.2 to about 10 wt %. The organic silicon compounds of this second group are selected from the group of methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and/or octadecyltriethoxysilane.

Even the addition of small amounts of water leads to hydrolysis in organic silicon compounds with at least one hydrolysable group. The hydrolysis products and/or organic silicon compounds having at least one hydroxy group may react with each other in a condensation reaction. For this reason, both the organosilicon compounds having at least one hydrolysable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolysable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly good results were obtained when organic silicon compounds of formula (I) and/or (II) were used in the process. Since, as previously described, hydrolysis/condensation already starts at traces of moisture, the condensation products of the organic silicon compounds (I) and/or (II) are also included in this embodiment.

Color-Forming Compounds (a2)

When agent (a) is applied to the keratinous material, the organic silicon compound(s) (a1) comprising one or more hydroxyl groups or hydrolysable groups per molecule are first hydrolyzed and oligomerized or polymerized in the presence of the water. The hydrolysis products or oligomers formed in this way have a particularly high affinity for the surface of the keratinous material. The simultaneous presence of the coloring compounds (a2) in the agent (a) integrates them into the resulting oligomers or polymers to form a colored film on the keratinous material. Following the application of agent (a), agent (b) is now applied. The successive application of agents (a) and (b) thus produces a coloration that is particularly resistant to external influences. The colorant compounds entrapped in these resistant films exhibit good wash fastness.

Thus, as an essential ingredient (a2) as contemplated herein, the agent (a) used in the dyeing process contains at least one colorant compound comprising at least one substrate platelet-based pigment comprising a vacuum metallized pigment.

The substrate platelets have an average thickness of at most about 50 nm, preferably less than about 30 nm, particularly preferably at most about 25 nm and especially preferably at most about 20 nm. The average thickness of the substrate platelets is at least about 1 nm, preferably at least about 2.5 nm, particularly preferably at least about 5 nm, for example at least about 10 nm. Preferred ranges for substrate platelet thickness are from about 2.5 to about 50 nm, from about 5 to about 50 nm, from about 10 to about 50 nm; from about 2.5 to about 30 nm, from about 5 to about 30 nm, from about 10 to about 30 nm; from about 2.5 to about 25 nm, from about 5 to about 25 nm, from about 10 to about 25 nm, from about 2.5 to about 20 nm, from about 5 to about 20 nm, and from about 10 to about 20 nm. Preferably, each substrate plate has a thickness that is as uniform as possible.

Due to the low thickness of the substrate platelets, the pigment exhibits particularly high hiding power.

The substrate plates have a monolithic structure. Monolithic in this context means consisting of a single closed unit without fractures, stratifications, or inclusions, although structural changes may occur within the substrate platelets. The substrate platelets are preferably homogeneously structured, i.e., there is no concentration gradient within the platelets. In particular, the substrate platelets do not have a layered structure and do not have any particles or particles distributed in them.

The size of the substrate platelet can be adjusted to the respective application purpose, especially the desired effect on the keratinic material. Typically, the substrate platelets have an average largest diameter of about 2 to about 200 μm, especially about 5 to about 100 μm.

In a preferred design, the aspect ratio, expressed by the ratio of the average size to the average thickness, is at least about 80, preferably at least about 200, more preferably at least about 500, more preferably more than about 750. The average size of the uncoated substrate platelets is the d50 value of the uncoated substrate platelets. Unless otherwise stated, the d50 value was determined using a Sympatec Helos device with quixel wet dispersion. To prepare the sample, the sample to be analyzed was pre-dispersed in isopropanol for 3 minutes.

The substrate platelets can be composed of any material that can be formed into platelet shape.

They can be of natural origin, but also synthetically produced. Materials from which the substrate platelets can be constructed include metals and metal alloys, metal oxides, preferably aluminum oxide, inorganic compounds, and minerals such as mica and (semi-)precious stones, and plastics. Preferably, the substrate platelets are constructed of metal (alloy).

Any metal suitable for metallic luster pigments can be used. Such metals include iron and steel, as well as all air and water resistant (semi)metals such as platinum, zinc, chromium, molybdenum and silicon, and their alloys such as aluminum bronzes and brass. Preferred metals are aluminum, copper, silver, and gold. Preferred substrate platelets include aluminum platelets and brass platelets, with aluminum substrate platelets being particularly preferred.

Vacuum metallized pigments (VMP) can be obtained, for example, by releasing metals, metal alloys or metal oxides from suitably coated films. They have a particularly low thickness of the substrate platelets in the range of from about 5 to about 50 nm and a particularly smooth surface with increased reflectivity. Substrate platelets comprising a vacuum metallized pigment are also referred to as VMP substrate platelets in the context of this application. VMP substrate platelets of aluminum can be obtained, for example, by releasing aluminum from metallized films.

The metal or metal alloy substrate plates can be passivated, for example by anodizing (oxide layer) or chromating.

Uncoated VMP substrate plates, especially those made of metal or metal alloy, reflect incident light to a high degree and produce a light-dark flop but no color impression.

A color impression can be created by optical interference effects, for example. Such pigments can be based on at least single-coated substrate platelets. These show interference effects by superimposing differently refracted and reflected light beams.

Accordingly, preferred pigments, pigments based on a coated VMP substrate platelet. The substrate platelet preferably has at least one coating B of a highly refractive metal oxide having a coating thickness of at least about 50 nm. There is preferably another coating A between the coating B and the surface of the substrate platelet. If necessary, there is a further coating C on the layer B, which is different from the layer B underneath.

Suitable materials for coatings A, B and C are all substances that can be applied to the substrate platelets in a film-like and permanent manner and, in the case of coatings A and B, have the required optical properties. Generally, coating part of the surface of the substrate platelets is sufficient to obtain a pigment with a glossy effect. For example, only the top and/or bottom of the substrate platelets may be coated, with the side surface(s) omitted. Preferably, the entire surface of the optionally passivated substrate platelets, including the side surfaces, is covered by coating B. The substrate platelets are thus completely enveloped by coating B. This improves the optical properties of the pigment and increases its mechanical and chemical resistance. The above also applies to layer A and preferably also to layer C if present.

Although multiple coatings A, B and/or C may be present in each case, the coated substrate platelets preferably have only one coating A, B and, if present, C in each case.

The coating B is composed of at least one highly refractive metal oxide. Highly refractive materials have a refractive index of at least about 1.9, preferably at least about 2.0, and more preferably at least about 2.4. Preferably, the coating B comprises at least about 95 wt %, more preferably at least about 99 wt %, of high refractive index metal oxide(s).

The coating B has a thickness of at least about 50 nm. Preferably, the thickness of coating B is no more than about 400 nm, more preferably no more than about 300 nm.

Highly refractive metal oxides suitable for coating B are preferably selectively light-absorbing (i.e., colored) metal oxides, such as iron(III) oxide ($\alpha$- and $\gamma$-Fe2O3, red), cobalt(II) oxide (blue), chromium(III) oxide (green), titanium(III) oxide (blue, usually present in admixture with titanium oxynitrides and titanium nitrides), and vanadium (V) oxide (orange), and mixtures thereof. Colorless high-index oxides such as titanium dioxide and/or zirconium oxide are also suitable.

Coating B may contain a selectively absorbing dye, preferably from about 0.001 to about 5% by weight, particularly preferably from about 0.01 to about 1% by weight, in each case based on the total amount of coating B. Suitable dyes are organic and inorganic dyes which can be stably incorporated into a metal oxide coating.

The coating A preferably has at least one low refractive index metal oxide and/or metal oxide hydrate. Preferably, coating A comprises at least about 95 wt %, more preferably at least about 99 wt %, of low refractive index metal oxide (hydrate). Low refractive index materials have a refractive index of about 1.8 or less, preferably about 1.6 or less.

Low refractive index metal oxides suitable for coating A include, for example, silicon (di)oxide, silicon oxide hydrate, aluminum oxide, aluminum oxide hydrate, boron oxide, germanium oxide, manganese oxide, magnesium oxide, and mixtures thereof, with silicon dioxide being preferred. The coating A preferably has a thickness of from about 1 to about 100 nm, particularly preferably from about 5 to about 50 nm, especially preferably from about 5 to about 20 nm.

Preferably, the distance between the surface of the substrate platelets and the inner surface of coating B is at most about 100 nm, particularly preferably at most about 50 nm, especially preferably at most about 20 nm. By ensuring that the thickness of coating A, and thus the distance between the surface of the substrate platelets and a coating B, is within the range specified above, it is possible to ensure that the pigments have a high hiding power.

If the pigment based on a VMP substrate platelet has only a layer A, it is preferred that the pigment has a VMP substrate platelet of aluminum and a layer A of silica. If the pigment based on a VMP substrate platelet has a layer A and a layer B, it is preferred that the pigment has a VMP substrate platelet of aluminum, a layer A of silica and a layer B of iron oxide.

According to a preferred embodiment, the pigments have a further coating C of a metal oxide (hydrate), which is different from the underlying coating B. Suitable metal oxides include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Silicon dioxide is preferred.

The coating C preferably has a thickness of from about 10 to about 500 nm, more preferably from about 50 to about 300 nm. By providing coating C, for example based on TiO2, better interference can be achieved while maintaining high hiding power.

Layers A and C serve as corrosion protection as well as chemical and physical stabilization. Particularly preferred layers A and C are silica or alumina applied by the sol-gel process. This process comprises dispersing the uncoated VMP substrate platelet or the VMP substrate platelet already coated with layer A and/or layer B in a solution of a metal alkoxide such as tetraethyl orthosilicate or aluminum triisopropanolate (usually in a solution of organic solvent or a mixture of organic solvent and water with at least about 50 wt. % organic solvent such as a C1 to C4 alcohol), and adding a weak base or acid to hydrolyze the metal alkoxide, thereby forming a film of the metal oxide on the surface of the (coated) substrate platelets.

Layer B can be produced, for example, by hydrolytic decomposition of one or more organic metal compounds and/or by precipitation of one or more dissolved metal salts, as well as any subsequent post-treatment (for example, transfer of a formed hydroxide-containing layer to the oxide layers by annealing).

Although each of the coatings A, B and/or C may be composed of a mixture of two or more metal oxide(hydrate) s, each of the coatings is preferably composed of one metal oxide(hydrate).

The pigments based on coated VMP substrate platelets preferably have a thickness of from about 70 to about 500 nm, particularly preferably from about 100 to about 400 nm, especially preferably from about 150 to about 320 nm, for example from about 180 to about 290 nm. Due to the low thickness of the substrate platelets, the pigment exhibits particularly high hiding power. The low thickness of the coated substrate platelets is achieved by keeping the thickness of the uncoated substrate platelets low, but also by adjusting the thicknesses of the coatings A and, if present, C to as small a value as possible. The thickness of coating B determines the color impression of the pigment.

The adhesion and abrasion resistance of pigments based on coated VMP substrate platelets in keratinic material can be significantly increased by additionally modifying the outermost layer, layer A, B or C depending on the structure, with organic compounds such as silanes, phosphoric acid esters, titanates, borates, or carboxylic acids. In this case, the organic compounds are bonded to the surface of the outermost, preferably metal oxide-containing, layer A, B, or C. The outermost layer denotes the layer that is spatially farthest from the VMP substrate platelet. The organic compounds are preferably functional silane compounds that can bind to the metal oxide-containing layer A, B, or C. These can be either mono- or bifunctional compounds. Examples of bifunctional organic compounds are methacryloxypropenyltrimethoxysilane, 3-methacryloxypropyltrimethoxysilane, 3-acryloxypropyltrimethoxysilane, 2-acryloxyethyltrimethoxysilane, 3-methacryloxypropyltriethoxysilane, 3-acryloxypropyltrimethoxysilane, 2-Methacryloxyethyltriethoxysilane, 2-acryloxyethyltriethoxysilane, 3-methacryloxypropyltris (methox-yethoxy) silane, 3-Methacryloxypropyltris (butoxyethoxy) silane, 3-methacryloxypropyltris (propoxy) silane, 3-methacryloxypropyltris (butoxy) silane, 3-acryloxypropyltris (methoxyethoxy) silane, 3-acryloxypropyltris (buttrimethoxy) silane, vinyl, propoxyethoxy) silane, vinyl, butoxyethoxy, tris (butoxyethoxy), vinyl, butoxyethoxy) silane, vinyl. Vinyltriethoxysilane, vinylethyl dichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, an alkylsilane or arylsilane, can be carried out. This has only one functional group, which can covalently bond to the surface pigment based on coated VMP substrate platelets (i.e., to the outermost metal oxide-containing layer) or, if not completely covered, to the metal surface. The hydrocarbon residue of the silane points away from the pigment. Depending on the type and nature of the hydrocarbon residue of the silane, a varying degree of hydrophobicity of the pigment is achieved. Examples of such silanes include hexadecyltrimethoxysilane, propyltrimethoxysilane, etc. Particularly preferred are pigments based on silica-coated aluminum substrate platelets surface-modified with a monofunctional silane. Octyltrimethoxysilane, octyltriethoxysilane, hecadecyltrimethoxysilane and hecadecyltriethoxysilane are particularly preferred. Due to the changed surface properties/hydrophobization, an improvement can be achieved in terms of adhesion, abrasion resistance and alignment in the application.

It has been shown that pigments based on VMP substrate platelets with such a surface modification also exhibit better compatibility with the organosilicon compounds used and/or their condensation or polymerization products.

Particularly good results were obtained if the agent (a)—based on the total weight of the agent (a)—contains one or more pigments based on a VMP substrate platelet in a total amount of from about 0.01 to about 10% by weight, preferably from about 0.1 to about 8% by weight, more preferably from about 0.2 to about 6% by weight and very preferably from about 0.5 to about 4.5% by weight.

Pigments based on a substrate platelet comprising a vacuum metallized pigment are available, for example, under the name Alegrace® Marvelous from the company Schlenk Metallic Pigments GmbH.

Pigments based on a VMP substrate platelet have a defined particle size in terms of thickness and particle area. This allows complete coverage of the keratinous material when used in the appropriate amount. In addition, dyeings with pigments based on VMP substrate platelets exhibit extremely high rub and wash fastness due to their smooth surface structure.

In addition to the pigment based on a VMP substrate platelet, the agent (a) may comprise further colorant compounds selected from the group of pigments and/or direct dyes.

The use of pigments has proved to be particularly preferable in this context.

In another very particularly preferred embodiment, the agent (a) comprises at least one further colorant compound (a2) from the group of pigments.

Pigments within the meaning of the present disclosure are coloring compounds which have a solubility in water at 25° C. of less than about 0.5 g/L, preferably less than about 0.1 g/L, even more preferably less than about 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, the composition (a) comprises at least one further colorant compound (a2) from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

Also preferred mica-based pigments are synthetically produced mica platelets coated with metal oxide, based on synthetic fluorophlogopite (INCI: Synthetic Fluorphlogopite). The synthetic fluorophlogopite platelets are coated, for example, with tin oxide, iron oxide(s) and/or titanium dioxide. The metal oxide layers may further contain pigments such as ferric hexacyanidoferrate(II/III) or carmine red. Such mica pigments are available, for example, under the name SYNCRYSTAL from Eckart.

In a further preferred embodiment, the agent (a) comprises at least one further colorant compound (a2) from the group of inorganic pigments selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, the agent (a) comprises at least one further colorant compound (a2) from the group of pigments selected from mica- or mica-based pigments which are reacted with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Other suitable pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

Examples of particularly suitable color pigments are commercially available under the trade names Rona®, Colorona®, Xirona®, Dichrona® and Timiron® from Merck, Anabel® and Unipure® from Sensient, Prestige® from Eckart Cosmetic Colors, Flamenco®, Cellini®, Cloisonne®, Duocrome®, Gemtone®, Timica®, MultiReflections, Chione from BASF SE and Sunshine® from Sunstar.

Particularly preferred color pigments with the trade name Colorona® are, for example:

Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)
Colorona SynCopper, Merck, Synthetic Fluorphlogopite (and) Iron Oxides
Colorona SynBronze, Merck, Synthetic Fluorphlogopite (and) Iron Oxides Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.
Xirona Le Rouge, Merck, Iron Oxides (and) Silica In addition, particularly preferred color pigments with the trade name Unipure® are for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

Also particularly preferred pigments with the trade name Flamenco® are, for example: Flamenco® Summit Turquoise T30D, BASF, Titanium Dioxide (and) Mica Flamenco® Super Violet 530Z, BASF, Mica (and) Titanium Dioxide In a further embodiment of the process, the agent (a) may also contain one or more colorant compounds from the group of organic pigments as a further colorant compound (a2).

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketo-pyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the composition (a) comprises at least one further colorant compound (a2) from the group of organic pigments selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As used herein, the term color varnish is understood to mean particles comprising a layer of absorbed dyes, the unit of particle and dye being insoluble under the above conditions. The particles may be, for example, inorganic substrates, which may be aluminum, silica, calcium borosilicate, calcium aluminum borosilicate, or aluminum.

For example, alizarin color varnish can be used.

Due to their excellent light and temperature stability, the use of the above pigments in agent (a) is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size D50 of from about 1 to about 50 µm, preferably from about 5 to about 45 µm, preferably from about 10 to about 40 µm, preferably from about 14 to about 30 µm. The mean particle size D50, for example, can be determined using dynamic light scattering (DLS).

In addition to the pigment based on a VMP substrate platelet, the agent (a) may contain as further colorant compound(s) (a2) other effect pigments such as pigments based on lamellar substrate platelets and/or pigments based on lenticular substrate platelets.

In a further preferred embodiment, the agent (a) contains—based on the total weight of the agent (a)—one or more further pigments in a total amount of from about 0.01 to about 10% by weight, preferably from about 0.1 to about 8% by weight, more preferably from about 0.2 to about 6% by weight and very particularly preferably from about 0.5 to about 4.5% by weight.

As further colorant compound(s) (a2), the agents (a) used in the process may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than about 0.5 g/L and are therefore not to be regarded as pigments. Preferably, the direct dyes within the meaning of the present disclosure have a solubility in water (760 mmHg) at 25° C. of more than about 1 g/L.

Direct dyes can be divided into anionic, cationic, and non-ionic direct dyes.

In a further preferred embodiment, the agent (a) comprises at least one anionic, cationic and/or nonionic direct dye as further coloring compound (a2).

In a further preferred embodiment, the agent (a) comprises at least one further colorant compound (a2) from the group of anionic, nonionic, and/or cationic direct dyes.

Suitable cationic direct dyes include Basic Blue 7, Basic Blue 26, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76 As non-ionic direct dyes, non-ionic nitro and quinone dyes and neutral azo dyes can be used.

Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

In the course of the work leading to the present disclosure, it has been found that dyeings of particularly high color intensity can be produced with agents (a) containing at least one anionic direct dye.

In an explicitly quite particularly preferred embodiment, the agent (a) further comprises at least one anionic direct dye.

Anionic direct dyes are also called acid dyes. Acid dyes are direct dyes that have at least one carboxylic acid group (—COOH) and/or one sulphonic acid group (—SO3H). Depending on the pH value, the protonated forms (—COOH, —SO3H) of the carboxylic acid or sulphonic acid groups are in equilibrium with their deprotonated forms (—OO—, —SO3-present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (760 mmHg) at 25° C. of more than about 0.5 g/L and are therefore not to be regarded as pigments. Preferably the acid dyes within the meaning of the present disclosure have a solubility in water (760 mmHg) at 25° C. of more than about 1 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In one embodiment, a process for dyeing keratinous material is thus preferred, in which the composition (a) further comprises at least one anionic direct dye selected from the group of nitrophenylenediamines, nitroaminophenols, azo dyes, anthraquinone dyes, triarylmethane dyes, xanthene dyes, rhodamine dyes, oxazine dyes and/or indophenol dyes, the xanthene dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO3H), a sodium sulfonate group (—SO3Na) and/or a potassium sulfonate group (—SO3K).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA no. B001), Acid Yellow 3 (COLIPA no. C 54, D&C Yellow No. 10, Quinoline Yellow, E104, Food Yellow 13), Acid Yellow 9 (CI 13015), Acid Yellow 17 (CI 18965), Acid Yellow 23 (COLIPA no. C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no. C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real red D, FD&C Red Nr. 2, Food Red 9, Naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no. 106 Pontacyl Brilliant Pink), Acid Red 73 (CI 27290), Acid Red 87 (Eosin, CI 45380), Acid Red 92 (COLIPA no. C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no. 2, C.I. 60730, COLIPA no. C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no. 401, Naphthalene Black 10B, Amido Black 10B, CI 20 470, COLIPA no. B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3 (2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalene-disulfonate and has a very high-water solubility of more than 20% by weight.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl) benzoic acid, whose solubility in water is indicated as greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a solubility in water of more than 20% by weight (25° C.).

In a highly preferred process the agent (a) contains at least one further colorant compound (a2) from the group of anionic direct dyes selected from the group of Acid Yellow 1, acid yellow 3, acid yellow 9, acid yellow 17, acid yellow 23, acid yellow 36, acid yellow 121, acid orange 6, acid orange 7, acid orange 10, acid orange 11, acid orange 15, acid orange 20, acid orange 24, acid red 14, acid red 27, acid red 33, acid red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in particular the anionic direct dyes, can be used in different amounts in the medium (a) depending on the desired color intensity. Particularly good results were obtained when the agent (a) contains—based on its total weight—one or more direct dyes (a2) in a total amount of from about 0.01 to about 10% by weight, preferably from about 0.1 to about 8% by weight, more preferably from about 0.2 to about 6% by weight and very particularly preferably from about 0.5 to about 4.5% by weight.

In a further preferred embodiment, the agent (a)—based on the total weight of the agent (a)—further comprises one or more direct dyes as further colorant compound (a2) in a total amount of from about 0.01 to about 10% by weight, preferably from about 0.1 to about 8% by weight, more preferably from about 0.2 to about 6% by weight and very preferably from about 0.5 to about 4.5% by weight.

Silicone Polymers (a3)

In another very particularly preferred embodiment, the agent (a) used in the process additionally contains at least one silicone polymer (a3).

Silicone polymers, which can alternatively be called silicones for short, are understood to be poly(organo)siloxanes. Silicone polymers are a group of synthetic polymers in which silicon atoms are linked via oxygen atoms.

Silicone polymers are generally macromolecules with a molecular weight of at least about 500 g/mol, preferably at least about 1000 g/mol, more preferably at least about 2500 g/mol, particularly preferably at least about 5000 g/mol, which comprise repeating organic units.

The maximum molecular weight of the silicone polymer depends on the degree of polymerization (number of polymerized monomers) and the batch size and is partly determined by the polymerization method. As contemplated herein, it is preferred if the maximum molecular weight of the silicone polymer is not more than 107 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups.

Corresponding to the high molecular weight of silicone polymers, these are based on more than about 10 Si—O repeat units, preferably more than about 50 Si—O repeat units, and more preferably more than about 100 Si—O repeat units, most preferably more than about 500 Si—O repeat units.

The silicone polymers (a3) contained in agent (a) are therefore different from the silanes (a1) also contained in agent (a).

In the context of one embodiment, a method for dyeing keratinous material is thus preferred, in which the agent comprises (a):
(a3) at least one silicone polymer.

In the work leading to the present disclosure, it was found that incorporation of the silicone polymer (a3) into the agent (a) resulted in an improvement in hair feel.

The film produced by the oligomerization or polymerization of the organosilicon compounds (silanes) (a1) may exhibit a certain stickiness or even softness, especially when higher amounts of silanes (a1) are used, which may have a detrimental effect on the feel of the keratinic materials on the one hand and on the durability of the film on the other. Without being committed to this theory, it is believed that the joint application of the silane (a1) and the silicone polymer (a3) in the medium (a) leads to a reaction or interaction of the two components with each other. When silane and silicone polymer are used together, the silanes appear to form a film, as previously described, into which the silicone polymers are either incorporated, or to which the silicone polymers agglomerate. It has been found that the film formed in this way is much more supple, flexible, durable, and less brittle.

Accordingly, it was observed that the rheological properties of the film produced by agent (a) could be greatly improved by the addition of at least one silicone polymer (a3). In the presence of the silicone polymers (a3), the film became firmer or more rigid, leaving the colored keratinous materials with a less sticky, smoother, and more pleasing appearance. Furthermore, the higher strength of the film also had positive effects on the fastness properties of the keratinic materials, especially on their rub fastness properties. Since the dyed films were more resistant when in contact with combs, brushes, and textiles, they showed less abrasion when in contact with these items.

When certain silicone polymers (a3) were used, the advantages described above were particularly pronounced. It has therefore been found to be particularly preferred if the agents (a) used in the process contain at least one alkoxy-modified silicone polymer and/or at least one amino-modified silicone polymer (a3).

In the context of one embodiment, a method for dyeing keratinous material is thus preferred, in which the agent comprises (a):
(a3) at least one alkoxy-modified and/or amino-modified silicone polymer.

In a further preferred embodiment, the agent (a) comprises at least one alkoxy-modified silicone polymer.

Alkoxy-modified silicones are silicones whose structure includes at least one structural alkoxy unit. This structural alkoxy unit can be, for example, an alkoxy group. Alkoxy groups are understood to be C2-C10 alkoxy groups. The alkoxy group may be terminal to the silicone (i.e., present, for example, as the group —O—CH3 or as the group —O—CH2-CH3). However, it is equally contemplated herein that in embodiments, the alkoxy group itself still carries a substituent; in this case, an alkoxy modification is understood to be at least one grouping located on the silicone such as, for example, (—CH2-CH2-O—), (—CH2-CH2-CH2-O—), (—CH(CH3)-CH2-O—), (—CH2-CH(CH3)-CH2-O—) or (—CH2-CH2-CH2-CH2-O—). Preferably, the alkoxy-modified silicones (A) carry at least one grouping (—CH2-CH2-O—) and/or (—CH2-CH2-CH2-O—).

The alkoxy groups may be linked to the silicone either via a carbon atom or via an oxygen atom, for example, the silicones may bear the structural units of the formula (S-a), (S-b), (S-c) and/or (S-d):

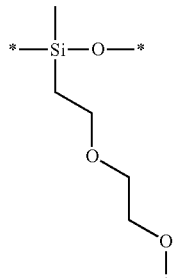

(Si-a)

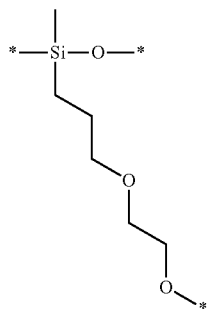

(Si-b)

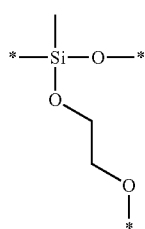

(Si-c)

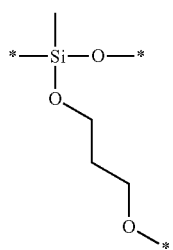

(Si-d)

It is particularly preferred if the alkoxy-modified silicone polymer(s) (a3) carry more than one alkoxy group, i.e., if the silicone polymers (a3) are polyalkoxylated. Polyalkoxylated silicones carry as structural units polyoxyalkylene groups, polyoxyethylene groups (i.e., groups of the type [—CH2-CH2-O—]m) and/or poloxypropylene groups (i.e., groups of the type [—CH(CH3)-CH2-O—]m and/or [—CH2-CH2-CH2-O—]m). Preferably, the number of polyoxyalkylene units in the silicone polymer is at least 2. Therefore, m is an integer greater than or equal to 2.

Particularly preferably, the alkoxy-modified silicone (a3) is a nonionic silicone. Non-ionic silicones carry neither positive nor negative charges.

Very particularly suitable polyalkoxylated silicones (a3) comprise at least one structural unit of the formula (S-I)

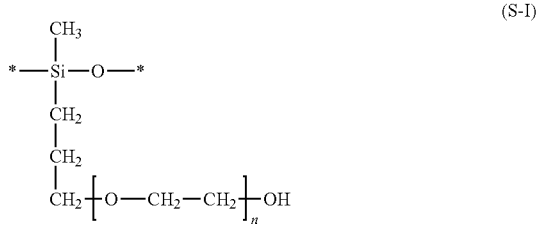

(S-I)

wherein
n is an integer from 2 to about 20, preferably an integer from about 4 to about 18, more preferably an integer from about 6 to about 16, still more preferably an integer from about 8 to about 14, and most preferably the number 12.

The positions marked with an asterisk * in the above formulas represent the free valences of the corresponding bonds, whereby the bond can be to a further Si atom, a further O atom and/or a further C atom.

In the context of one embodiment, a method for dyeing keratinous material is thus preferred, in which the agent comprises (a):

(a3) at least one silicone polymer comprising at least one structural unit of formula (S-I)

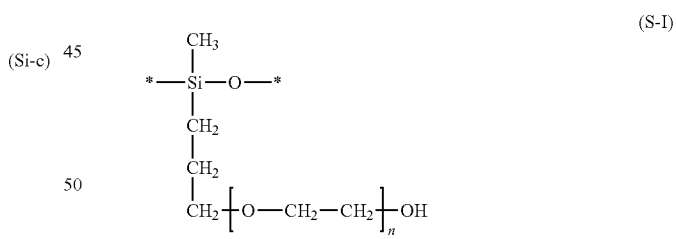

(S-I)

wherein
n is an integer from 2 to about 20, preferably an integer from about 4 to about 18, more preferably an integer from about 6 to about 16, still more preferably an integer from about 8 to about 14, and most preferably the number 12.

A preferred alkoxy-modified silicone polymer (a3) may contain, in addition to one or more structural units of the general formula (S-I), further structural units that differ structurally from the units of formula (S-I). Particularly preferably, the alkoxy-modified silicone polymer additionally comprises one or more dimethylsiloxane units. Depending on whether the silicone is linear or branched, it has two (in the case of a chain linear silicone) or more (in the case of a branched silicone) end groups. It has been found to be particularly advantageous if a silicone polymer (a3) as contemplated herein has a trimethylsilyloxy group (i.e., a group —O—Si(CH3)3) as end groups in each case.

In a further particularly preferred embodiment, the agent (a) comprises at least one silicone polymer (a3) which is composed of structural units of the formula (S-I), the formula (S-II), the formula (S-III) and the formula (S-IV),

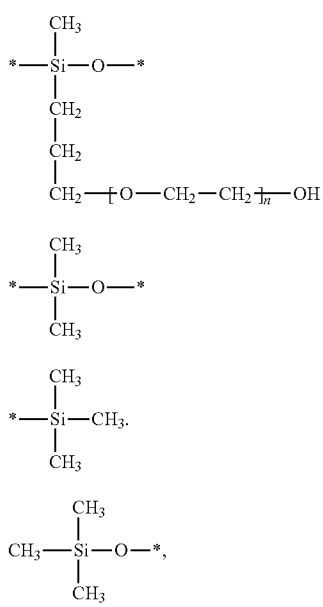

wherein n—independently in each structural unit (S-I)—represents in each case an integer from 2 to about 20, preferably an integer from about 4 to about 18, more preferably an integer from about 6 to about 16, still more preferably an integer from about 8 to about 14, and most preferably the number 12.

A silicone polymer (a3) composed of structural units of the formula (S-I), the formula (S-II), the formula (S-III) and the formula (S-IV) is understood in this context to mean a silicone which exclusively possesses (in each case one or more) structural units of the formulae (S-I), (S-II), (S-III) and (S-IV). Here, the silicone can also contain different structural units of the formula (S-I), each of which is distinguished by its number n.

The positions marked with an asterisk in the structural units each represent the linkage points to the other structural units. For example, a very particularly preferred silicone polymer (a3) composed of structural units of formula (S-I), formula (S-II), formula (S-III) and formula (S-IV) may have the following structure:

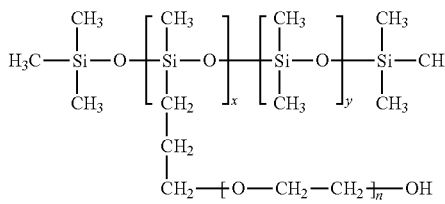

x and y are chosen here depending on the desired molecular weight of the silicone, and n represents one of the preferred or particularly preferred integers described above.

Both low molecular weight and higher molecular weight alkoxy-modified silicones can be used as silicone polymers (a3). Particularly beneficial effects were observed for silicone polymers (a3) with a molar mass of from about 800 to about 10,000 g/mol, preferably of from about 1,000 to about 9,000 g/mol, further preferably of from about 2,000 to about 8,000 g/mol and especially preferably of from about 2,500 to about 5,000 g/mol.

Particularly well-suited silicone polymers include:
Abil B 8843 from Evonik, PEG-14 DIMETHICONE
Xiameter OFX 0193 Fluid by comoany Dow Corning, PEG-12 Dimethicone Furthermore, particularly good results were also obtained when an agent (a) containing an amino-modified silicone polymer (a3) was used in the process. The amino-modified silicone polymer may alternatively be referred to as an amino-functionalized silicone polymer or also as an amino silicone.

In another preferred embodiment, the agent (a) comprises at least one amino-modified silicone polymer.

Agent (a) may contain one or more different amino-modified silicone polymers (a3). Such silicones can be exemplified by the formula (S-V)

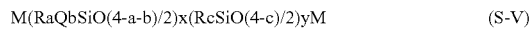

$$M(R_aQ_bSiO_{(4-a-b)/2})_x(R_cSiO_{(4-c)/2})_yM \quad (S\text{-}V)$$

in which formula above R is a hydrocarbon or a hydrocarbon radical having from 1 to about 6 carbon atoms, Q is a polar radical of the general formula —R1HZ wherein R1 is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl, and the like; and sulfur-containing radicals, such as mercaptoethyl, mercaptopropyl, mercaptohexyl, mercaptophenyl, and the like; preferably R is an alkyl radical containing from 1 to about 6 carbon atoms, and most preferably R is methyl. Examples of R1 include methylene, ethylene, propylene, hexamethylene, decamethylene, —CH2CH(CH3)CH2-, phenylene, naphthylene, —CH2CH2SCH2CH2-, —CH2CH2OCH2-, —OCH2CH2-, —OCH2 CH2CH2-, CH2CH(CH3)C (O)OCH2-, —(CH2)3CC(O)OCH2CH2-, —C6H 4C6H4-, —C6H 4CH2C6H4- and —(CH2)3C(O) SCH2CH2-.

Z is an organic amino functional residue containing at least one amino functional group. One possible formula for Z is NH(CH2)zNH2, where z is 1 or more. Another possible formula for Z is —NH(CH2)z(CH 2)zzNH, wherein both z and zz are independently 1 or more, this structure comprising diamino ring structures, such as piperazinyl. Z is most preferably an —NHCH2CH2NH2 residue. Another possible formula for Z is —N(CH2)z(CH2)zzNX2 or —NX2, wherein each X of X2 is independently selected from the group of hydrogen and alkyl groups having 1 to about 12 carbon atoms, and zz is 0.

Q is most preferably a polar, amine-functional radical of the formula —CH2CH2CH2NHCH2CH2NH2. In the formulas, "a" takes values ranging from about 0 to about 2, "b" takes values ranging from about 2 to about 3, "a"+"b" is less than or equal to 3, and "c" is a number ranging from about 1 to about 3. The molar ratio of RaQb SiO(4−a−b)/2 units to RcSiO (4-c)/2 units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone blend.

In a particularly preferred embodiment, the application of an agent (a) to the keratinous material, wherein the agent (a) is an amino-modified silicone polymer of formula (S-VI)

R'aG3-a-Si(OSiG2)n-(OSiG2bR'2-b)m-O-SiG3-a-R'a (S-VI), wherein:
G is —H, a phenyl group, OH, —O—CH3, —CH3, —O—CH2CH3, —CH2CH3, —O—CH2CH2CH3, —CH2CH2CH3, —O—CH(CH3)2, —CH(CH3)2, —O—CH2CH2CH2CH3, —CH2CH2CH2CH3, —O—CH2CH(CH3)2, —CH2CH(CH3)2, —O—CH(CH3)CH2CH3, —CH(CH3)CH2CH3, —O-C(CH3)3, —C(CH3)3;
a stands for a number between 0 and 3, especially 0;
b stands for a number between 0 and 1, especially 1,
m and n are numbers whose sum (m+n) is between 1 and about 2000, preferably between about 50 and about 150, where n preferably assumes values from 0 to about 1999 and from about 49 to about 149 and m preferably assumes values from 1 to about 2000, preferably from 1 to about 10,
R' is a monovalent radical selected from
Q-N(R")—CH2-CH2-N(R")2
Q-N(R")2
Q-N+(R")3A-
Q-N+H(R")2 A-
Q-N+H2(R")A-
Q-N(R")—CH2-CH2-N+R"H2A-,
where each Q is a chemical bond, —CH2-, —CH2-CH2-, —CH2CH2CH2-, —C(CH3)2-, —CH2CH2CH2CH2-, —CH2C(CH3)2-, —CH(CH3) CH2CH2-,
R" represents identical or different radicals selected from the group of —H, -phenyl, -benzyl, —CH2-CH(CH3) Ph, the C1-20 alkyl radicals, preferably —CH3, —CH2CH3, —CH2CH2CH3, —CH(CH3)2, —CH2CH2CH2H3, —CH2CH(CH3)2, —CH(CH3) CH2CH3, —C(CH3)3, and A represents an anion preferably selected from chloride, bromide, iodide or methosulfate.

In another preferred embodiment, an agent (a) is applied to the keratinous material, wherein the agent (a) comprises at least one amino-modified silicone polymer (a3) of formula (S-VII),

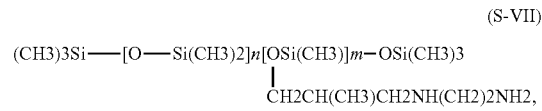
(S-VII)

wherein m and n are numbers whose sum (m+n) is between 1 and about 2000, preferably between about 50 and about 150, n preferably assuming values from 0 to about 1999 and from about 49 to about 149, and m preferably assuming values from 1 to about 2000, preferably from 1 to about 10.

According to the INCI declaration, these silicones are called trimethylsilylamodimethicones.

In another preferred embodiment, an agent (a) is applied to the keratinous material, wherein the agent (a) comprises at least one amino-modified silicone polymer (a3) of formula (S-VIII)

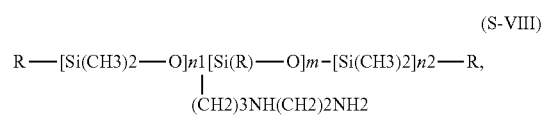
(S-VIII)

in which R represents —OH, —O—CH3 or a —CH3 group and m, n1 and n2 are numbers whose sum (m+n1+n2) is between 1 and about 2000, preferably between about 50 and about 150, the sum (n1+n2) preferably assuming values from 0 to about 1999 and from about 49 to about 149 and m preferably assuming values from 1 to about 2000, preferably from 1 to about 10.

According to the INCI declaration, these amino-modified or amino-functionalized silicone polymers are known as amodimethicones.

Regardless of which amino-modified silicones are used, agents (a) containing an amino-modified silicone polymer whose amine number is above about 0.25 meq/g, preferably above about 0.3 meq/g and above about 0.4 meq/g, are preferred. The amine number represents the milliequivalents of amine per gram of the amino-functional silicone. The amine number represents the milliequivalents of amine per gram of the amino-functional silicone.

In another preferred embodiment, an agent (a) is applied to the keratinous material, wherein the agent (a) comprises at least one amino-modified silicone polymer (a3) of the formula of formula (S-IX),

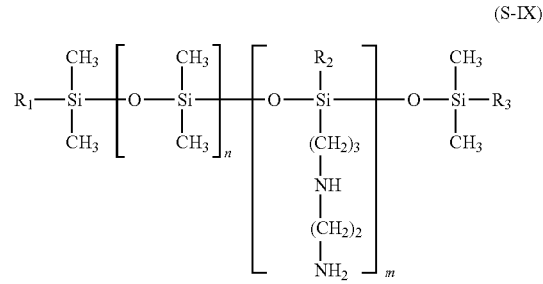
(S-IX)

where
- m and n mean numbers chosen so that the sum (n+m) is in the range of from 1 to about 1000,
- n is a number in the range of from 0 to about 999 and m is a number in the range of from 1 to about 1000,
- R1, R2 and R3, which are the same or different, denote a hydroxy group or a C1-4 alkoxy group,
- wherein at least one of R1 to R3 represents a hydroxy group;

Other preferred methods include applying an agent (a) to the keratinous material, said agent (a) comprising at least amino-functional silicone polymer of the formula of the formula (S-X)

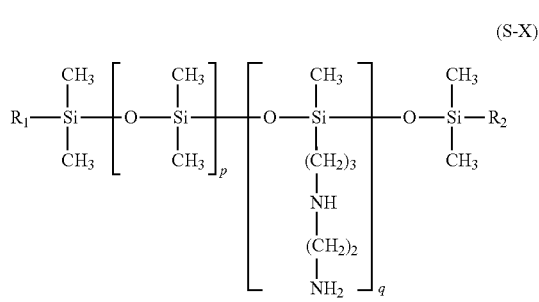

(S-X)

in which
- p and q mean numbers chosen so that the sum (p+q) is in the range of from 1 to about 1000,
- p is a number in the range 0 to 999 and q is a number in the range of from 1 to about 1000,
- R1 and R2, which are different, denote a hydroxy group or a C1-4 alkoxy group, at least one of R1 to R2 denoting a hydroxy group.

The silicones of the formulas (S-IX) and (S-X) differ in the grouping at the Si atom carrying the nitrogen-containing group: In formula (S-IX), R2 represents a hydroxy group or a C1-4 alkoxy group, while the residue in formula (S-X) is a methyl group. The individual Si groupings, which are marked with the indices m and n or p and q, do not have to be present as blocks; rather, the individual units can also be present in a statistically distributed manner, i.e., in the formulas (S-IX) and (S-X), not every RT-Si(CH3)2 group is necessarily bound to an —[O—Si(CH3)2] grouping.

Processes in which an agent (a) containing at least one amino-modified silicone polymer (a3) of the formula of the formula (S-XI) is applied to the keratin fibers have also proved to be particularly effective regarding the desired effects

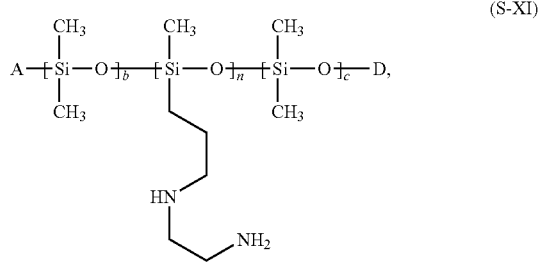

(S-XI)

located in the
A represents a group —OH, —O—Si(CH3)3, —O—Si(CH3)2OH, —O—Si(CH3)2OCH3, D represents a group —H, —Si(CH3)3, —Si(CH3)2OH, —Si(CH3)2OCH3, b, n, and c stand for integers between 0 and about 1000, with the specifications
- n>0 and b+c>0
- at least one of the conditions A=—OH or D=—H is fulfilled.

In the above formula (S-XI), the individual siloxane units are statistically distributed with the indices b, c, and n, i.e., they do not necessarily have to be block copolymers.

Particularly good effects regarding the improvement of rub fastness were observed when an agent (a) containing a special 4-morpholinomethyl-substituted silicone polymer (a3) was applied to the keratinous material in the procedures. This very particularly preferred amino-functionalized silicone polymer comprises at least one structural unit of the formula (S-XIII)

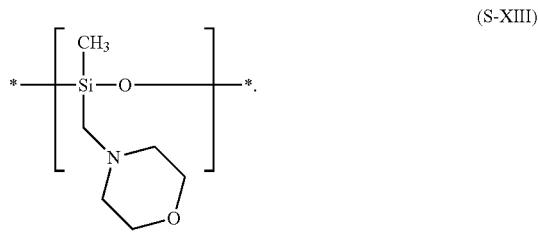

(S-XIII)

In the context of one embodiment, a method for dyeing keratinous material is thus preferred, in which the agent comprises (a):

(a3) at least one silicone polymer comprising at least one structural unit of the formula (S-XIII)

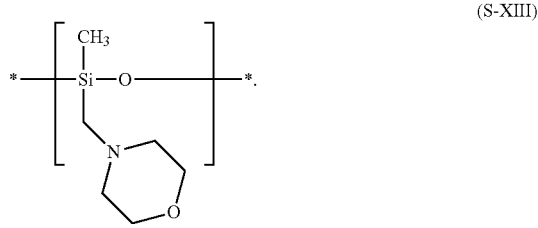

(S-XIII)

Particularly good effects in terms of improving rub fastness were also observed when an agent (a) containing a special 4-morpholinomethyl-substituted silicone polymer (a3) was applied to the keratinous material in the procedures. This very particularly preferred amino-functionalized silicone polymer comprises structural units of the formulae (S-XII) and of the formula (S-XIII)

(S-XII)

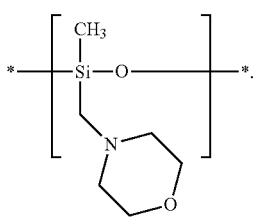
(S-XIII)

In an explicitly quite particularly preferred embodiment, the agent (a) contains at least one amino-modified silicone polymer (a3) which comprises structural units of the formula (S-XII) and of the formula (S-XIII)

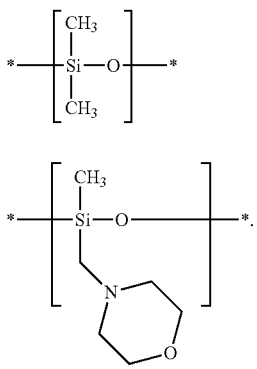

Corresponding 4-morpholinomethyl-substituted silicone polymers are described below.

A very particularly preferred amino-functionalized silicone polymer is known as amodimethicone/morpholinomethyl silsesquioxane copolymer and is commercially available in the form of the raw material Belsil ADM 8301 E from Wacker.

As a 4-morpholinomethyl-substituted silicone, for example, a silicone can be used which has structural units of the formulae (S-XII), (S-XIII') and (S-XIV')

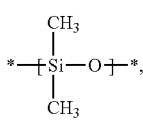
(S-XII)

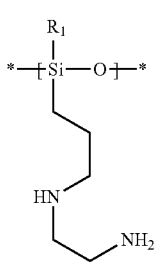
(S-XIV')

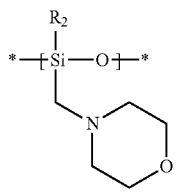
(S-XIII')

in which
R1 is —CH3, —OH, —OCH3, —O—CH2CH3, —O—CH2CH2CH3, or —O—CH(CH3)2;
R2 is —CH3, —OH, or —OCH3.

Particularly preferred compositions (a) as contemplated herein contain at least one 4-morpholinomethyl-substituted silicone of the formula (S-XV)

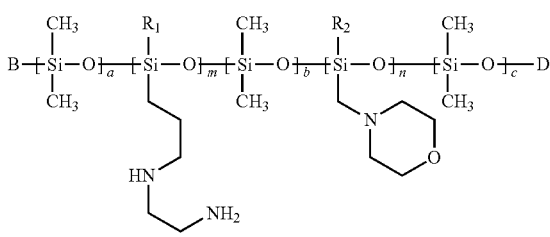
(S-V)

located in the
R1 is —CH3, —OH, —OCH3, —O—CH2CH3, —O—CH2CH2CH3, or —O—CH(CH3)2;
R2 is —CH3, —OH, or —OCH3.
B represents a group —OH, —O—Si(CH3)3, —O—Si(CH3)2OH, —O—Si(CH3)2OCH3,
D represents a group —H, —Si(CH3)3, —Si(CH3)2OH, —Si(CH3)2OCH3,
a, b, and c stand independently for integers between 0 and about 1000, with the condition a+b+c>0
m and an independently of each other stand for integers between 1 and about 1000 with the proviso that
at least one of the conditions B=—OH or D=—H is fulfilled,
the units a, b, c, m, and n are distributed statistically or blockwise in the molecule.

Structural formula (Si-VI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m, and n are preferably statistically distributed.

The silicones used as contemplated herein represented by formula (Si-VI) can be trimethylsilyl-terminated (D or B=—Si(CH3)3), but they can also be dimethylsilylhydroxy-terminated on two sides or dimethylsilylhydroxy-terminated and dimethylsilylmethoxy-terminated on one side. Silicones particularly preferred as contemplated herein are selected from silicones in which
B=—O—Si(CH3)2OH and D=—Si(CH3)3
B=—O—Si(CH3)2OH and D=—Si(CH3)2OH
B=—O—Si(CH3)2OH and D=—Si(CH3)2OCH3

B=—O—Si(CH3)3 and D=—Si(CH3)20H
B=—O—Si(CH3)20CH3 and D=—Si(CH3)20H
to everyone.

To produce particularly resistant films, the agent (a) contains the silicone polymer(s), in particular the alkoxy-modified and/or the amino-modified silicone polymers, preferably in specific ranges of amounts.

Particularly flexible films of low tack were obtained when an agent (a) was used in the process which contains—based on the total weight of the agent (a)—one or more silicone polymers (a3) in a total amount of from about 0.1 to about 8% by weight, preferably from about 0.1 to about 5% by weight, more preferably from about 0.1 to about 3% by weight and very particularly preferably from about 0.1 to about 0.5% by weight.

In the context of a further preferred embodiment, the agent (a) contains—based on the total weight of the agent (a)—one or more silicone polymers in a total amount of from about 0.1 to about 15% by weight, preferably from about 0.5 to about 12% by weight, more preferably from about 1 to about 10% by weight and most preferably from about 2 to about 8% by weight.

In an explicitly quite particularly preferred embodiment, the agent (a) contains—based on the total weight of the agent (a)—one or more alkoxy-modified silicone polymers in a total amount of from about 0.1 to about 15% by weight, preferably from about 0.5 to about 12% by weight, more preferably from about 1 to about 10% by weight, and most preferably from about 2 to about 8% by weight.

In the context of an explicitly quite particularly preferred embodiment, the agent (a) contains—based on the total weight of the agent (a)—one or more amino-modified silicone polymers in a total amount of from about 0.1 to about 15% by weight, preferably from about 0.5 to about 12% by weight, more preferably from about 1 to about 10% by weight and very particularly preferably from about 2 to about 8% by weight.

pH Value of the Agent (a)

It has been found preferable if the agent (a) is made up in the form of a water-containing agent adjusted to an alkaline pH.

To adjust the pH value, the agent (a) may contain at least one alkalizing agent.

To adjust the desired pH, the agents (a) may therefore also contain at least one alkalizing agent. The pH values for the purposes of the present disclosure are pH values measured at a temperature of 22° C.

As alkalizing agent, agent (a) may contain, for example, ammonia, alkanolamines and/or basic amino acids.

The alkanolamines that can the agent in the compositions are preferably selected from primary amines having a C2-C6 alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Particularly preferred alkanolamines are selected from 2-aminoethan-1-ol and/or 2-amino-2-methylpropan-1-ol. In a particularly preferred embodiment the agent as contemplated herein contains an alkanolamine selected from 2-aminoethan-1-ol and/or 2-amino-2-methylpropan-1-ol as alkalizing agent.

As contemplated herein, an amino acid is an organic compound containing in its structure at least one protonatable amino group and at least one —COOH or one —SO3H group. Preferred amino acids are aminocarboxylic acids, especially α-(alpha)-aminocarboxylic acids and ω-aminocarboxylic acids, whereby α-aminocarboxylic acids are particularly preferred.

Basic amino acids are those amino acids which have an isoelectric point pI greater than about 7.

Basic α-aminocarboxylic acids contain at least one asymmetric carbon atom. As contemplated herein, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In a further particularly preferred embodiment, the alkalizing agent is a basic amino acid selected from the group of arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Although the agents (a) are preferably adjusted to pH values in the alkaline range, it may nevertheless be necessary in principle to also use acidifiers in small quantities for fine adjustment of the desired pH value. Suitable acidifiers are, for example, citric acid, lactic acid, acetic acid or also dilute mineral acids (such as hydrochloric acid, sulfuric acid, phosphoric acid).

However, in the course of the work leading to the present disclosure, it has been found that the presence of the alkalizing agent or the adjustment of the alkaline pH is essential for the formation of resistant films on the keratinous material. The presence of excessive amounts of acids can have a negative effect on the strength of the films. For this reason, it has proved preferable to keep the quantities of acids used in the medium (a) as low as possible. For this reason, it is advantageous if the total amount of organic and/or inorganic acids contained in the agent (a) does not exceed a certain value.

In a further preferred embodiment, the total amount of organic acids from the group of citric acid, tartaric acid, malic acid, and lactic acid contained in the agent (a) is below about 1% by weight, preferably below about 0.7% by weight, more preferably below about 0.5% by weight, even more preferably below about 0.1% by weight and most preferably below about 0.01% by weight.

In a further preferred embodiment, the total amount of inorganic acids from the group of hydrochloric acid, sulfuric acid and phosphoric acid contained in the agent (a) is below about 1% by weight, preferably below about 0.7% by weight, more preferably below about 0.5% by weight, still more preferably below about 0.10% by weight and very particularly preferably below about 0.01% by weight.

The maximum total amounts of the acids contained in the agent (a) given above are always based on the total weight of the agent (a).

Agent (b)

The method of treatment of keratinous material includes, in addition to the application of agent (a), the application of agent (b). The agent (b) used in the process contains at least one sealing reagent (b1).

The agent (b) is a post-treatment agent and the application of agent (b) to the keratinous material treated with agent (a) has the effect of making the colorations obtained in the process more durable. In particular, the use of agent (b) can improve the fastness to washing and the fastness to rubbing of the dyeings obtained in the process.

It is preferred that the sealing reagent (b1) comprises a compound selected from the group of film-forming polymers, alkalizing agents, acidifying agents, and mixtures thereof.

It may be preferred that the sealing reagent (b1) comprises a film-forming polymer.

Polymers are macromolecules with a molecular weight of at least about 1000 g/mol, preferably of at least about 2500 g/mol, particularly preferably of at least about 5000 g/mol, which consist of identical, repeating organic units. The polymers as contemplated herein may be synthetically produced polymers which are manufactured by polymerization of one type of monomer or by polymerization of different types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. In terms of the present disclosure, it is preferred if the maximum molecular weight of the film-forming hydrophobic polymer is not more than 107 g/mol, preferably not more than 106 g/mol, and particularly preferably not more than 105 g/mol.

As contemplated herein, a film-forming polymer is a polymer which can form a film on a substrate, for example on a keratinic material or a keratinic fiber. The formation of a film can be demonstrated, for example, by viewing the polymer-treated keratinous material under a microscope.

The film-forming polymers in agent (b) can be hydrophilic or hydrophobic.

In a first embodiment, it may be preferred to use at least one hydrophobic film-forming polymer as sealing reagent (b1) in agent (b).

A hydrophobic polymer is a polymer that has a solubility in water at 25° C. (760 mmHg) of less than about 1% by weight.

The water solubility of the film-forming, hydrophobic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers, and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, the agent (b) comprises at least one film-forming, hydrophobic polymer as sealing reagent (b1), which is selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable.

Other particularly well-suited film-forming hydrophobic polymers can be selected from the homopolymers or copolymers of olefins, such as cycloolefins, butadiene, isoprene or styrene, vinyl ethers, vinyl amides, the esters, or amides of (meth)acrylic acid having at least one C1-C20 alkyl group, an aryl group or a C2-C10 hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate), isopentyl (meth)acrylate, n-butyl (meth)acrylate), isobutyl (meth)acrylate, ethyl (meth)acrylate, methyl (meth)acrylate, tert-butyl (meth) acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, those with C2-C18 alkyl groups, such as N-ethyl acrylamide, N-tert-butylacrylamide, le N-octylacrylamide, N-di(C1-C4)alkyl(meth)acrylamide.

Other preferred anionic copolymers are, for example, copolymers of acrylic acid, methacrylic acid or their C1-C6 alkyl esters, as they are marketed under the INCI Declaration Acrylates Copolymers. A suitable commercial product is for example Aculyn® 33 from Rohm & Haas. Copolymers of acrylic acid, methacrylic acid or their C1-C6 alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25

Methacrylate Copolymer), Structure 2001® (Acryla-tes/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme und Haas distributed Soltex OPT (Acrylates/C12-22 Alkyl methacrylate Copolymer).

Suitable polymers based on vinyl monomers may include, for example, the homopolymers and copolymers of N-vinylpyrrolidone, vinylcaprolactam, vinyl-(C1-C6)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable olefin-based polymers include homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers containing one or more blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Surprisingly, it was found that particularly intense and washfast colorations could be obtained when agent (b) contained at least one film-forming polymer as sealing reagent (b1), which was selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, the agent (b) comprises at least one film-forming polymer as sealing agent (b1), which is selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer as sealing reagent (b1) in agent (b).

A hydrophilic polymer is a polymer that has a solubility in water at 25° C. (760 mmHg) of more than about 1% by weight, preferably more than about 2% by weight.

The water solubility of the film-forming, hydrophilic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1% by weight.

Nonionic, anionic, and cationic polymers can be used as film-forming, hydrophilic polymers.

Suitable film-forming hydrophilic polymers may be selected, for example, from the group of polyvinylpyrrolidone (co)polymers, polyvinyl alcohol (co)polymers, vinyl acetate (co)polymers, the carboxyvinyl (co)polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-containing copolymer as film-forming hydrophilic polymer.

In another very particularly preferred embodiment, the agent (b) comprises at least one film-forming, hydrophilic polymer as sealing reagent (b1), which is selected from the group of polyvinylpyrrolidone (PVP) and the copolymers of polyvinylpyrrolidone.

It is further preferred if the agent contains polyvinylpyrrolidone (PVP) as the film-forming hydrophilic polymer. Surprisingly, the wash fastness of the stains obtained with PVP-containing agents (b) was also particularly good.

Particularly well-suited polyvinylpyrrolidones are available, for example, under the name Luviskol® K from BASF SE, especially Luviskol® K 90 or Luviskol® K 85 from BASF SE.

The polymer PVP K30, which is marketed by Ashland (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF.

The use of film-forming hydrophilic polymers as sealing reagent (b1) from the group of copolymers of polyvinylpyrrolidone also led to particularly good and washfast color results.

Vinylpyrrolidone-vinyl ester copolymers, such as those marketed under the trademark Luviskol® (BASF), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-containing copolymer.

Other suitable copolymers of polyvinylpyrrolidone may also be those obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In another very particularly preferred embodiment, the agent (b) comprises at least one film-forming, hydrophilic polymer as sealing reagent (b1), which is selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another fussy copolymer of vinylpyrrolidone is the polymer known under the INCI designation maltodextrin/VP copolymer.

Furthermore, intensively colored keratinous material, especially hair, could be obtained with particularly good wash fastness properties when a nonionic film-forming hydrophilic polymer was used as the film-forming hydrophilic polymer.

In another embodiment, the agent (b) may comprise at least one nonionic, film-forming, hydrophilic polymer as sealing reagent (b1).

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products containing, as a non-ionic, film-forming, hydrophilic polymer, at least one polymer selected from the group of Polyvinylpyrrolidone, Copolymers of N-vinylpyrrolidone and vinyl esters of carboxylic acids containing 2 to 18 carbon atoms of N-vinylpyrrolidone and vinyl acetate, Copolymers of N-vinylpyrrolidone and N-vinylimidazole and methacrylamide, Copolymers of N-vinylpyrrolidone and N-vinylimidazole and acrylamide, Copolymers of N-vinylpyrrolidone with N,N-di(C1 to C4)alkylamino-(C2 to C4)alkyl acrylamide.

If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from about 20:80 to about 80:20, in particular from about 30:70 to about 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF SE.

Another particularly preferred polymer is selected from the INCI designation VP/Methacrylamide/Vinyl Imidazole Copolymer, which is available under the trade name Luviset Clear from BASF SE.

Another particularly preferred nonionic, film-forming, hydrophilic polymer is a copolymer of N-vinylpyrrolidone and N,N-dimethylaminiopropylmethacrylamide, which is sold, for example, by ISP under the INCI designation VP/DMAPA Acrylates Copolymer, e.g., under the trade name Styleze® CC 10.

A cationic polymer is the copolymer of N-vinylpyrrolidone, N-vinylcaprolactam, N-(3-dimethylaminopropyl) methacrylamide and 3-(methacryloylamino)propyl-lauryl-dimethylammonium chloride (INCI designation: Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include

Vinylpyrrolidone-vinylimidazolium methochloride copolymers, as offered under the designations Luviquat® FC 370, FC 550 and the INCI designation Polyquaternium-16 as well as FC 905 and HM 552, Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available for example under the name Luviquat® Hold from BASF SE. Polyquaternium-46 is preferably used in an amount of from about 1 to about 5% by weight—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol or under the names Synthalen M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers prepared from monomers of (meth)acrylamido-C1-C4-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of poly(meth)arylamido-C1-C4-alkyl-sulfonic acids are crosslinked and at least 90% neutralized. These polymers can be crosslinked or non-crosslinked.

Cross-linked and fully or partially neutralized polymers of the poly-2-acrylamido-2-methylpropane sulfonic acid type are available under the INCI names "Ammonium Poly acrylamido-2-methyl-propanesulphonates" or "Ammonium Poly acryldimethyltauramides".

Another preferred polymer of this type is the crosslinked poly-2-acrylamido-2methyl-propanesulfonic acid polymer sold by Clariant under the trade name Hostacerin AMPS, which is partially neutralized with ammonia.

In another explicitly very particularly preferred embodiment, the agent (b) comprises at least one anionic, film-forming, polymer as sealing reagent (b1).

In this context, the best results were obtained when the agent (b) contains, as sealing reagent (b1), at least one film-forming polymer comprising at least one structural unit of formula (P-I) and at least one structural unit of formula (P-II)

where
M is a hydrogen atom or ammonium (NH4), sodium, potassium, ½ magnesium or ½ calcium.

In a further preferred embodiment, the agent (b) comprises at least one film-forming polymer as sealing reagent (b1), which comprises at least one structural unit of the formula (P-I) and at least one structural unit of the formula (P-II)

where
M is a hydrogen atom or ammonium (NH4), sodium, potassium, ½ magnesium or ½ calcium.

When M represents a hydrogen atom, the structural unit of the formula (P-I) is based on an acrylic acid unit.

When M stands for an ammonium counterion, the structural unit of the formula (P-I) is based on the ammonium salt of acrylic acid.

When M stands for a sodium counterion, the structural unit of the formula (P-I) is based on the sodium salt of acrylic acid.

When M stands for a potassium counterion, the structural unit of the formula (P-I) is based on the potassium salt of acrylic acid.

If M stands for a half equivalent of a magnesium counterion, the structural unit of the formula (P-I) is based on the magnesium salt of acrylic acid.

If M stands for a half equivalent of a calcium counterion, the structural unit of the formula (P-I) is based on the calcium salt of acrylic acid.

The film-forming polymer or polymers are preferably used in specific ranges of amounts in the agent (b). In this context, it has proved particularly preferable if the agent (b) contains—based on the total weight of the agent (b)—one or more film-forming polymers as sealing reagent (b1) in a total amount of from about 0.1 to about 18% by weight, preferably from about 1 to about 16% by weight, more preferably from about 5 to about 14.5% by weight and very particularly preferably from about 8 to about 12% by weight.

In a further preferred embodiment, the agent (b) contains—based on the total weight of the agent (b)—one or more film-forming polymers as sealing reagent (b1) in a total amount of from about 0.1 to about 18% by weight, preferably from about 1 to about 16% by weight, more preferably from about 5 to about 14.5% by weight and very particularly preferably from about 8 to about 12% by weight.

The application of agent (b) comprising a film-forming polymer as sealing reagent (b1) is intended to seal and/or fix the colored film initially produced by the application of agent (a). With application of the second agent (b) with a film-forming polymer as sealing reagent (b1), the film-forming polymer is deposited on the colored film produced in the first layer in the form of a further film. The multilayer film system created in this way exhibits improved resistance to external influences.

Here, the film produced by the agent (b) comprising a film-forming polymer as sealing reagent (b1) is preferably not colored itself. In this way, it can also be ensured that any abrasion to a certain extent of the second film formed by agent (b) does not lead to any color changes in the entire film system. It is therefore particularly preferred if the agent (b) contains no or only small amounts of colorant compounds.

In an alternative embodiment, the sealing reagent (b1) contains an alkalizing agent.

Particularly preferably, the alkalizing agent is selected from the group of ammonia, C2-C6 alkanolamines, basic amino acids, alkali metal hydroxides and alkaline earth metal hydroxides.

In another particularly preferred embodiment, the agent (b) contains at least one alkalizing agent as sealing reagent (b1), which is selected from the group of ammonia, C2-C6 alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates and alkaline earth metal carbonates.

It has been found that aftertreatment with an agent (b) containing ammonia exerts a particularly good influence on improving the wash fastness and rub fastness of the dyeings obtained in the process.

In the context of a further very particularly preferred embodiment, the composition (b) comprises ammonia as sealing reagent (b1).

Good results were also obtained when composition (b) contained at least one C2-C6 alkanolamine as sealing reagent (b1).

The alkanolamines that can be used in composition (b) can be selected, for example, from the group of primary amines having a C2-C6 alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4- ol, 3-amino-2-methylpropan-1-ol, 1-amino-2-methylpropan-2-ol, 3-aminopropan-1,2-diol, 2-amino-2-methylpropan-1,3-diol.

In a further preferred embodiment, the composition (b) comprises, as sealing reagent (b1), at least one alkalizing agent from the group of alkanolamines, which is preferably selected from the group of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol and 2-amino-2-methylpropane-1,3-diol.

Likewise, good results were obtained when composition (b) contained at least one basic amino acid as sealing reagent (b1).

As contemplated herein, an amino acid is an organic compound containing in its structure at least one protonatable amino group and at least one —COOH or one —SO3H group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than about 7.0.

Basic α-aminocarboxylic acids contain at least one asymmetric carbon atom. As contemplated herein, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In a further particularly preferred embodiment, the sealing reagent (b1) is an alkalizing agent comprising a basic amino acid selected from the group of arginine, lysine, ornithine and/or histidine.

In a further preferred embodiment, the agent (b) comprises as sealing reagent (b1) at least one alkalizing agent selected from the group of basic amino acids, which is preferably selected from the group of arginine, lysine, ornithine, and histidine.

Good results were also obtained when the agent (b) contained at least one alkali metal hydroxide as sealing reagent (b1). Examples of well-suited alkali metal hydroxides are sodium hydroxide and potassium hydroxide.

Good results were also obtained when the composition (b) contained, as sealing reagent (b1), an alkalizing agent comprising at least one alkaline earth metal hydroxide. Suitable alkaline earth metal hydroxides include magnesium hydroxide, calcium hydroxide and barium hydroxide.

Good results were also obtained when the agent (b) contained at least one alkali metal silicate and/or alkali metal metasilicate as sealing reagent (b1). Suitable alkali metal silicates include sodium silicate and potassium silicate. Suitable alkali metal metasilicates include sodium metasilicate and potassium metasilicate.

Good results were also obtained when the agent (b) contained at least one alkali metal carbonate and/or alkaline earth metal carbonate as sealing reagent (b1). Suitable alkali metal carbonates include sodium carbonate and potassium carbonate. Suitable alkaline earth metal carbonates include magnesium carbonate and calcium carbonate.

Within the group of the sealing reagents (b1) in the form of an alkalizing agent, ammonia, C2-C6 alkanolaminenes, basic amino acids and alkali metal hydroxides have proved to be particularly suitable.

In the context of a further particularly preferred embodiment, the agent (b) comprises as sealing reagent (b1) at least one alkalizing agent selected from the group of ammonia, C2-C6 alkanolamines, basic amino acids and alkali metal hydroxides.

In another particularly preferred embodiment, the agent (b) comprises, as sealing reagent (b1), at least one alkalizing agent selected from the group of ammonia, 2-aminoethan-1-ol, 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide and potassium hydroxide.

Composition (b) contains the alkalizing agent as a sealing reagent (b1) in a cosmetic carrier, preferably in an aqueous cosmetic carrier.

In this context, it has been found preferable if the agent (b) contains—based on the total weight of the agent (b)—from about 5.0 to about 99.0% by weight, preferably from about 15.0 to about 97.0% by weight, more preferably from about 25.0 to about 97.0% by weight, still more preferably from about 35.0 to about 97.0% by weight and very particularly preferably from about 45.0 to about 97.0% by weight of water.

In the context of a further embodiment, the agent (b) contains—based on the total weight of the agent (b)—from about 5.0 to about 99.0% by weight, preferably from about 15.0 to about 97.0% by weight, more preferably from about 25.0 to about 97.0% by weight, still more preferably from about 35.0 to about 97.0% by weight and very particularly preferably from about 45.0 to about 97.0% by weight of water.

The alkalizing agents contained in the agent (b) exert an influence on the pH value of the agent (b). It was found that certain alkaline pH values have a beneficial effect on the dyeing performance achievable in the process and the fastness properties of the dyeings.

For this reason, it is preferred that the agent (b) comprising an alkalizing agent as sealing reagent (b1) has a pH of from about 7.0 to about 12.0, preferably from about 7.5 to about 11.5, more preferably from about 8.0 to about 11.0, and most preferably from about 8.5 to about 9.5.

The pH value can be measured using the usual methods known from the state of the art, such as pH measurement using glass electrodes via combination electrodes or using pH indicator paper.

In another very particularly preferred embodiment, the agent (b) contains an alkalizing agent as sealing reagent (b1) and has a pH of from about 7.0 to about 12.0, preferably from about 7.5 to about 11.5, more preferably from about 8.0 to about 11.0 and most preferably from about 8.5 to about 9.5.

The pH values as contemplated herein are pH values measured at a temperature of 22° C.

In a still further alternative embodiment, the sealing reagent (b1) contains an acidifying agent.

Particularly preferably, the acidifying agent is selected from the group of inorganic acids, organic acids, and mixtures thereof.

Good results could be obtained when agent (b) contains at least one inorganic acid as sealing reagent (b1). Suitable inorganic acids are, for example, phosphoric acid, sulfuric acid and/or hydrochloric acid, with sulfuric acid being particularly preferred.

In a further preferred embodiment, the agent (b) comprises, as sealing reagent (b1), at least one acidifying agent selected from the group of inorganic acids, which is preferably selected from the group of phosphoric acid, sulfuric acid, hydrochloric acid, and mixtures thereof.

In a further, even more preferred embodiment, the agent (b) contains sulfuric acid as sealing reagent (b1).

Good results were also obtained when agent (b) contained at least one organic acid as sealing reagent (b1). The organic acid is preferably selected from the group of formic acid, acetic acid, propionic acid, butyric acid, isobutyric acid, valeric acid, isovaleric acid, pivalic acid, oxalic acid, malonic acid, succinic acid, glutaric acid, glyceric acid, Glyoxylic acid, adipic acid, pimelic acid, corkic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluoylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-napthalenepentaacetic acid, malonaldehyde acid, 4-hydroxy-phthalamic acid, 1-pyrazolecarboxylic acid, gallic acid or propane tricarboxylic acid, glycolic acid, gluconic acid, lactic acid, maleic acid, ascorbic acid, malic acid, tartaric acid, citric acid and mixtures thereof.

In a further preferred embodiment, the agent (b) comprises as sealing reagent (b1) at least one acidifying agent selected from the group of organic acids, wherein the organic acid is preferably selected from the group of formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, corkic acid, azelaic acid, sebacic acid, propiolic acid, crotonic acid, isocrotonic acid, elaidic acid, Maleic acid, fumaric acid, muconic acid, citraconic acid, mesaconic acid, camphoric acid, benzoic acid, o,m,p-phthalic acid, naphthoic acid, toluoylic acid, hydratropasic acid, atropasic acid, cinnamic acid, isonicotinic acid, nicotinic acid, bicarbamic acid, 4,4'-dicyano-6,6'-binicotinic acid, 8-carbamoyloctanoic acid, 1,2,4-pentane tricarboxylic acid, 2-pyrrole carboxylic acid, 1,2,4,6,7-napthalene pentaacetic acid, malonaldehyde acid, 4-hydroxy-phthalamic acid, 1-pyrazole carboxylic acid, gallic acid or propane tricarboxylic acid, glycolic acid, gluconic acid, lactic acid, maleic acid, ascorbic acid, malic acid, tartaric acid, citric acid and mixtures thereof.

In a further, even more preferred embodiment, the agent (b) contains acetic acid as sealing reagent (b1).

Also, suitable acidifiers include methanesulfonic acid and/or 1-hydroxyethane-1,1-diphosphonic acid.

Within the group of the above-mentioned sealing reagents (b1) in the form of an acidifying agent, sulfuric acid and/or acetic acid have proved to be particularly suitable.

In the context of a further particularly preferred embodiment, the agent (b) comprises as sealing reagent (b1) at least one acidifying agent selected from the group of sulfuric acid, acetic acid, and mixtures thereof.

The agent (b) contains the acidifying agent as sealing reagent (b1) in a cosmetic carrier, preferably in an aqueous cosmetic carrier.

The acidifying agents contained in the agent (b) exert an influence on the pH of the agent (b). It was found that acidic pH values also have a beneficial effect on the dyeing performance achievable in the process and the fastness properties of the dyeings.

For this reason, it is preferred that the agent (b) comprising an acidifying agent as sealing reagent (b1) has a pH of from about 2.0 to about 6.5, preferably from about 3.0 to about 6.0, more preferably from about 4.0 to about 6.0, and most preferably from about 4.5 to about 5.5.

The pH value can be measured using the usual methods known from the state of the art, such as pH measurement using glass electrodes via combination electrodes or using pH indicator paper.

In another very particularly preferred embodiment, the agent (b) contains an acidifying agent as sealing reagent (b1) and has a pH of from about 2.0 to about 6.5, preferably from about 3.0 to about 6.0, more preferably from about 4.0 to about 6.0, and most preferably from about 4.5 to about 5.5.

The pH values as contemplated herein are pH values measured at a temperature of 22° C.

Other Ingredients in Products (a) and (b)

The agents (a) and (b) described above may also contain one or more optional ingredients.

The products may also contain one or more surfactants. The term surfactants refer to surface-active substances. A distinction is made between anionic surfactants consisting of a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO(-)— or —SO3(-) group in the molecule. Particularly suitable zwitterionic surfactants are the so-called betaines such as the N-alkyl-N,N-dimethylammoniumglycinate, for example the cocoalkyl-dimethylammoniumglycinate, N-acylaminopropyl-N,N-dimethyl-ammoniumglycinate, for example, cocoacylaminopropyl dimethyl ammonium glycinate, and 2-alkyl-3-carboxymethyl-3-hydroxyethyl imidazolines each having from about 8 to about 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, in addition to a C8-C24 alkyl or acyl group in the molecule, contain at least one free amino group and at least one —COOH or —SO3H group and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to about 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocosalkylaminopropionate, cocoacylaminoethylaminopropionate and C12-C18-acylsarcosine.

The products may also additionally contain at least one non-ionic surfactant. Suitable non-ionic surfactants are alkyl polyglycosides as well as alkylene oxide addition products to fatty alcohols and fatty acids with from about 2 to about 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually consisting of a hydrocarbon backbone (e.g., consisting of one or two linear or branched alkyl chains) and the positive charge(s) being in the hydrophilic head group. Examples of cationic surfactants are quaternary ammonium compounds which may carry one or two alkyl chains with a chain length of from about 8 to about 28 carbon atoms as hydrophobic radicals, quaternary phosphonium salts substituted by one or more alkyl chains having a chain length of from about 8 to about 28 carbon atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of from about 0.1 to about 45 wt. %, preferably from about 1 to about 30 wt. % and most preferably from about 1 to about 15 wt. %—based on the total weight of the respective agent.

Furthermore, the agents may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with from about 12 to about 20 C atoms in the alkyl group and up to about 16 glycol ether groups in the molecule.

The anionic surfactants are used in a total quantity of from about 0.1 to about 45 wt. %, preferably from about 1 to about 30 wt. % and most preferably from about 1 to about 15 wt. %—based on the total weight of the respective agent.

The agent (a) and/or agent (b) may further comprise a matting agent. Suitable matting agents include, for example, (modified) starches, waxes, talc and/or (modified) silicas. The amount of matting agent is preferably between about 0.1 and about 10% by weight based on the total amount of agent (a) or agent (b). Preferably, agent (a) contains a matting agent.

The agents may also contain other active ingredients, auxiliaries and additives, such as solvents; fatty ingredients such as C8-C30 fatty acid triglycerides, C8-C30 fatty acid monoglycerides, C8-C30 fatty acid diglycerides and/or the hydrocarbons; structurants such as glucose, maleic acid and lactic acid, hair-conditioning compounds such as phospholipids, for example lecithin and kephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of from about 0.0001 to about 25 wt. % each, preferably from about 0.0005 to about 15 wt. %, based on the total weight of the respective agent.

Process for Dyeing Keratinous Materials

In the procedure as contemplated herein, agents (a) and (b) are applied to the keratinous materials, to human hair. Thus, agents (a) and (b) are the ready-to-use agents. The agents (a) and (b) are different.

In principle, agents (a) and (b) can be applied simultaneously or successively, whereby successive application is preferred.

The best results were obtained when agent (a) was first applied to the keratinous materials in a first step and agent (b) was applied in a second step.

Quite particularly preferred, therefore, is a process for treating keratinous material, for coloring keratinous material, in particular human hair, comprising the following steps in the order indicated:

in a first step, applying an agent (a) to the keratinous material, the agent comprising (a):

(a1) at least one organic silicon compound selected from the group of silanes having one, two or three silicon atoms, and (a2) at least one colorant compound comprising at least one substrate platelet-based pigment comprising a vacuum metallized pigment, and In a second step, applying an agent (b) to the keratinous material, the agent comprising (b):

(b1) at least one sealing reagent.

Moreover, to impart a high leaching resistance to the dyed keratinous material over a longer period, agents (a) and (b) are particularly preferably applied within one and the same dyeing process, which means that there is a period of a maximum of several hours between the application of agents (a) and (b).

In a further preferred embodiment, the agent (a) is applied first and agent (b) is applied thereafter, the period between the application of agents (a) and (b) being at most about 24 hours, preferably at most about 12 hours and particularly preferably at most about 6 hours.

A distinguishing feature of the agent (a) is its content of at least one reactive organic silicon compound (a1). The reactive organic silicon compound(s) (a1) undergoes an oligomerization or polymerization reaction and thus functionalizes the hair surface as soon as it meets it. In this way, a first, film is formed. The coloring compounds (a2) are incorporated into the film so that it is colored. In the second step of the process, a second agent (b) is now applied to the hair. During the application of the agent (b) comprising at least one film-forming polymer as sealing reagent (b1), the latter interacts with the silane film and is thus bound to the keratinous materials. During the application of agent (b) comprising at least one alkalizing agent or acidifying agent as sealing reagent (b1), the formation of the silane film is positively influenced.

In the context of a further form of execution, a procedure comprising the following steps in the order indicated is particularly preferred
- (1) Application of the agent (a) on the keratinous material,
- (2) Allow the agent (a) to act for a period of from about 10 seconds to about 10 minutes, preferably from about 10 seconds to about 5 minutes,
- (3) if necessary, rinse the keratinous material with water,
- (4) Application of agent (b) on the keratinous material,
- (5) Allowing the agent (b) to act for a period of from about 30 seconds to about 30 minutes, preferably from about 30 seconds to about 10 minutes,
- (6) Rinse the keratinous material with water.

The rinsing of the keratinous material with water in steps (3) and (6) of the process is understood, as contemplated herein, to mean that only water is used for the rinsing process, without any other agents other than agents (a) and (b).

In step (1), agent (a) is first applied to the keratinous materials, in particular human hair.

After application, the agent (a) is left to act on the keratinous materials. In this context, application times from about 10 seconds to about 10 minutes, preferably from about 20 seconds to about 5 minutes and especially preferably from about 30 seconds to about 2 minutes on the hair have proven to be particularly beneficial.

In a preferred embodiment, the agent (a) can now be rinsed from the keratinic materials before the agent (b) is applied to the hair in the subsequent step.

Stains with equally good wash fastnesses were obtained when agent (b) was applied to the keratinous materials that were still exposed to agent (a).

In step (4), agent (b) is now applied to the keratinous materials. After application, let the agent (b) act on the hair.

Even with a short contact time of the agent (b), the process allows the production of dyeings with particularly good intensity and wash fastness. Application times from about 10 seconds to about 10 minutes, preferably from about 20 seconds to about 5 minutes and most preferably from about 30 seconds to about 3 minutes on the hair have proven to be particularly beneficial.

In step (6), the agent (b) (and any agent (a) still present) is now rinsed out of the keratinous material with water.

In this embodiment, the sequence of steps (1) to (6) preferably takes place within about 24 hours.

Agent (a) contains, with the organic silicon compound(s), a class of highly reactive compounds that can undergo hydrolysis or oligomerization and/or polymerization when used.

As a result of their high reactivity, these organic silicon compounds form a film on the keratinous material.

To avoid premature oligomerization or polymerization, it is of considerable advantage to the user to prepare the ready-to-use agent (a) only shortly before application.

In yet another embodiment, preferred is a method comprising the following steps in the order indicated.
- (1) Preparation of an agent (a) by mixing a first agent (a') and a second agent (a"), wherein
  - the first agent (a') comprises at least one organic silicon compound (a1) from the group of silanes having one, two or three silicon atoms, and
  - the second agent (a") comprises at least one colorant compound (a2) comprising at least one pigment based on a substrate platelet comprising a vacuum metallized pigment,
- (2) Application of the agent (a) on the keratinous material,
- (3) Allow the agent (a) to act for a period of from about 10 seconds to about 10 minutes, preferably from about 10 seconds to about 5 minutes,
- (4) if necessary, rinse the keratinous material with water,
- (5) Application of agent (b) on the keratinous material,
- (6) Allowing the agent (b) to act for a period of from about 30 seconds to about 30 minutes, preferably from about 30 seconds to about 10 minutes,
- (7) Rinse the keratinous material with water.

To be able to provide a formulation that is as stable as possible in storage, the agent (a') itself is preferably formulated to be low in water or water-free.

In a preferred embodiment, a multicomponent packaging unit (kit-of-parts) is provided in which the agent (a')—based on the total weight of the agent (a')—contains a water content of from about 0.001 to about 10% by weight, preferably from about 0.5 to about 9% by weight, more preferably from about 1 to about 8% by weight and very particularly preferably from about 1.5 to about 7% by weight.

The agent (a") contains water. In a preferred embodiment, a multicomponent packaging unit (kit-of-parts) is provided in which the agent (a")—based on the total weight of the agent (a2)—has a water content of from about 15 to about 100% by weight, preferably from about 35 to about 100% by weight, more preferably from about 55 to about 100% by weight, still more preferably from about 65 to about 100% by weight and very particularly preferably from about 75 to about 100% by weight.

Within this embodiment, the ready-to-use agent (a) is now prepared by mixing agents (a') and (a").

For example, the user may first stir or shake the agent (a') containing the organic silicon compound(s) (a1) with the aqueous colorant-containing agent (a"). The user can now apply this mixture of (a') and (a") to the keratinous materials—either immediately after its preparation or after a short reaction time of from about 10 seconds to about 20 minutes. Afterwards, the user can apply agent (b) as described above.

The optionally included silicone polymer (a3) may be included in the agent (a') or in the agent (a"). Preferably, the silicone polymer (a3) is contained in the agent (a").

In yet another embodiment, preferred is a method comprising the following steps in the order indicated.
- (1) Preparation of an agent (a) by mixing a first agent (a') and a second agent (a"), wherein
  - the first agent (a') comprises at least one organic silicon compound (a1) from the group of silanes having one, two or three silicon atoms and furthermore at least one silicone polymer (a3), and
  - the second agent (a") comprises at least one colorant compound (a2) comprising at least one pigment based on a substrate platelet comprising a vacuum metallized pigment,
- (2) Application of the agent (a) on the keratinous material,
- (3) Allow the agent (a) to act for a period of from about 10 seconds to about 10 minutes, preferably from about 10 seconds to about 5 minutes, (4) if necessary, rinse the keratinous material with water,
(5) Application of agent (b) on the keratinous material,
(6) Allowing the agent (b) to act for a period of from about 30 seconds to about 30 minutes, preferably from about 30 seconds to about 10 minutes,
(7) Rinse the keratinous material with water.

In the context of a further embodiment, particularly preferred is a method comprising the following steps in the order indicated.

(1) Preparation of an agent (a) by mixing a first agent (a') and a second agent (a"), wherein
  the first agent (a') comprises at least one organic silicon compound (a1) from the group of silanes having one, two or three silicon atoms, and
  the second agent (a") comprises at least one colorant compound (a2) comprising at least one pigment based on a substrate platelet comprising a vacuum metallized pigment, and further comprises at least one silicone polymer (a3),
(2) Application of the agent (a) on the keratinous material,
(3) Allow the agent (a) to act for a period of from about 10 seconds to about 10 minutes, preferably from about 10 seconds to about 5 minutes,
(4) if necessary, rinse the keratinous material with water,
(5) Application of agent (b) on the keratinous material,
(6) Allowing the agent (b) to act for a period of from about 30 seconds to about 30 minutes, preferably from about 30 seconds to about 10 minutes,
(7) Rinse the keratinous material with water.

In a further preferred embodiment, the silicone polymer(s) (a3) are provided in a third separately prepared agent (a''').

Preferred in the context of this further embodiment is a method comprising the following steps in the order indicated.

(1) Preparation of an agent (a) by mixing a first agent (a') and a second agent (a") and
  a third agent (a"), wherein
  the first agent (a') comprises at least one organic silicon compound (a1) from the group of silanes having one, two or three silicon atoms, and
  the second agent (a") comprises at least one colorant compound (a2) comprising at least one pigment based on a substrate platelet comprising a vacuum metallized pigment, and
  the third agent (a"') comprises at least one silicone polymer (a3),
(2) Application of the agent (a) on the keratinous material,
(3) Allow the agent (a) to act for a period of from about 10 seconds to about 10 minutes, preferably from about 10 seconds to about 5 minutes,
(4) if necessary, rinse the keratinous material with water,
(5) Application of agent (b) on the keratinous material,
(6) Allowing the agent (b) to act for a period of from about 30 seconds to about 30 minutes, preferably from about 30 seconds to about 10 minutes,
(7) Rinse the keratinous material with water.

Multi-Component Packaging Unit (Kit-of-Parts)

To increase user comfort, the user is preferably provided with all required resources in the form of a multi-component packaging unit (kit-of-parts).

A second subject matter as contemplated herein is therefore a multi-component packaging unit (kit-of-parts) for coloring keratinic material, comprehensively packaged separately from one another a first container comprising an agent (a'), wherein the agent comprises (a'):
  (a1) at least one organic silicon compound selected from the group of silanes having one, two or three silicon atoms, and
a second container comprising an agent (a"), wherein the agent comprises (a"):
  (a2) at least one colorant compound comprising at least one substrate platelet-based pigment comprising a vacuum metallized pigment, and
a third container containing an agent (b), wherein the agent contains (b):
  (b1) at least one sealing reagent,
wherein the components (a1), (a2) and (b1) have been disclosed in detail above.

The organic silicon compounds (a1) from the group of silanes with one, two or three silicon atoms contained in agent (a) of the kit correspond to the organic silicon compounds that were also used in agent (a) of the previously described process.

The colorant compound (a2) contained in the agent (a") of the kit, comprising at least one substrate platelet-based pigment comprising a vacuum metallized pigment, correspond to the VMP substrate platelet-based pigments also used in the agent (a) of the previously described process.

The sealing reagent (b1) contained in agent (b) of the kit corresponds to the sealing reagent that was also used in agent (b) of the previously described method.

In this context, it is again possible to use the optionally included silicone polymer (a3) To be made up in the agent (a'), in the agent (a") or in a further agent (a''').

In the context of a further embodiment, a multi-component packaging unit (kit-of-parts) for coloring keratinic material is preferably packaged separately from one another
  a first container comprising an agent (a'), wherein the agent comprises (a'):
  at least one organic silicon compound (a1) from the group of silanes with one, two or three silicon atoms and furthermore at least one silicone polymer (a3), and
  a second container comprising an agent (a"), the agent comprising (a"):
  (a2) at least one colorant compound comprising at least one substrate platelet-based pigment comprising a vacuum metallized pigment, and
  a third container containing an agent (b), wherein the agent contains (b):
  (b1) at least one sealing reagent,
  wherein the components (a1), (a2), (a3) and (b1) have been disclosed in detail above.

In the context of a further embodiment, a multi-component packaging unit (kit-of-parts) for coloring keratinic material is preferably packaged separately from one another
  a first container comprising an agent (a'), wherein the agent comprises (a'): at least one organic silicon compound (a1) from the group of silanes with one, two or three silicon atoms and furthermore at least one silicone polymer (a3), and
  a second container comprising an agent (a"), the agent comprising (a"):
  (a2) at least one colorant compound comprising at least one substrate platelet-based pigment comprising a vacuum metallized pigment, and
  a third container containing an agent (a'''), wherein the agent (a''') is a water-containing cosmetic carrier
  a fourth container containing agent (b), wherein the agent contains (b):
  (b1) at least one sealing reagent,
  wherein the components (a1), (a2), (a3) and (b1) have been disclosed in detail above.

In this embodiment, agents (a') and (a") have a low water content. To prepare the ready-to-use agent (a), agents (a'), (a") and (a''') are mixed. In this case, the agent (a") represents a water-containing cosmetic carrier.

In the context of a further embodiment, a multi-component packaging unit (kit-of-parts) for coloring keratinic material is preferably packaged separately from one another
- a first container comprising an agent (a'), wherein the agent comprises (a'):
- at least one organic silicon compound (a1) from the group of silanes having one, two or three silicon atoms,
- a second container comprising an agent (a"), wherein the agent comprises (a"):
- (a2) at least one colorant compound comprising at least one substrate platelet-based pigment comprising a vacuum metallized pigment, and further comprising at least one silicone polymer (a3), and
- a third container containing an agent (b), wherein the agent contains (b):
- (b1) at least one sealing reagent,
- wherein the components (a1), (a2), (a3) and (b1) have been disclosed in detail above.

In the context of a further embodiment, a multi-component packaging unit (kit-of-parts) for coloring keratinic material is preferably packaged separately from one another
- a first container comprising an agent (a'), wherein the agent comprises (a'):
- at least one organic silicon compound (a1) from the group of silanes having one, two or three silicon atoms,
- a second container comprising an agent (a"), the agent comprising (a"):
- (a2) at least one colorant compound comprising at least one substrate platelet-based pigment comprising a vacuum metallized pigment,
- a third container comprising an agent (a"), said agent comprising (a"):
- at least one silicone polymer (a3), and
- a fourth container containing agent (b), wherein the agent contains (b):
- (b1) at least one sealing reagent,
- wherein the components (a1), (a2), (a3) and (b1) have been disclosed in detail above.

Concerning the further preferred embodiments of the multicomponent packaging unit, mutatis mutantis what has been said about the process applies.

EXAMPLES

Example 1

The following formulations have been produced (unless otherwise indicated, all figures are in % by weight)

| Agent (a') | |
|---|---|
| Agent (a') | in wt.. % |
| (3-Aminopropyl)triethoxysilane (a1) | 20 |
| Methyltrimethoxysilane (a1) | 70 |
| Water | ad 100 |

| Agent (a") | |
|---|---|
| Agent (a") | in wt.. % |
| Alegrace ® Marvelous 01-03 (Schlenk Metallic Pigments) (a2) | 5 |
| PEG-12 Dimethicone (a3) | 5 |
| Hydroxyethyl cellulose | 1 |
| Water | ad 100 |

The ready-to-use agent (a) was prepared by mixing 5 g of agent (a') and 20 g of agent (a"). The pH value of the agent (a) was adjusted to a value of 10.5 by adding ammonia or lactic acid. Then the agent (a) was allowed to stand for about 5 minutes.

| Agent (b) | |
|---|---|
| Agent (b) | in wt.. % |
| Ethylene/Sodium Acrylate Copolymer (b1) (25% solution) | 40 |
| Water | ad 100 |

The agent (a) was massaged into one strand of hair at a time (Kerling, Euronatural hair white), and left to act for 1 minute. The agent (a) was then rinsed with water.

Subsequently, agent (b) was applied to the hair strand, left to act for 1 minute and then also rinsed with water.

Subsequently, the strands were visually evaluated. A whitish metallic coloring of the hair with high intensity and fastness was obtained.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the following steps:
    applying an agent (a) to the keratinous material, wherein the agent (a) comprises:
    (a1) at least one organic silicon compound selected from the group of silanes having one, two or three silicon atoms, and
    (a2) at least one colorant compound comprising at least one substrate platelet-based pigment comprising a vacuum metallized pigment, and
    applying an agent (b) to the keratinous material, wherein the agent (b) comprises:
    (b1) at least one sealing reagent.

2. The process according to claim 1, wherein the agent (a) comprises at least one organic silicon compound (a1) of the formula (I) and/or (II)

$$R_1R_2N\text{-}L\text{-}Si(OR_3)_a(R_4)_b \qquad (I),$$

where
- $R_1$, $R_2$ independently represent a hydrogen atom or a $C_1$-$C_6$ alkyl group,
- L is a linear or branched divalent $C_1$-$C_{20}$ alkylene group,
- $R_3$, $R_4$ independently of one another represent a $C_1$-$C_6$ alkyl group,
- a, stands for an integer from 1 to 3, and
- b stands for the integer 3-a, and wherein in the organic silicon compound of formula (II)

$(R_5O)_c(R_6)_d$ Si-(A)$_e$-NR$_7$-(A')]$_f$-[O-(A")]$_g$-[NR$_8$- (A''')]$_h$-Si(R$_6$')$_d$(OR$^{5'}$)$_{c'}$ (II),

- R5, R5', R5", R6, R6' and R6" independently represent a $C_1$-$C_6$ alkyl group,
- A, A', A", A''' and A"" independently represent a linear or branched divalent $C_1$-$C_{20}$ alkylene group,
- $R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

-(A"")-Si(R$_6$")$_d$"(OR$_5$")$_{c''}$ (III),

- c stands for an integer from 1 to 3,
- d stands for the integer 3-c,
- c" stands 'for an integer from 1 to 3,
- d' stands for the integer 3-c',
- c" stands, for an integer from 1 to 3,
- d" stands for the integer 3-c",
- e stands for 0 or 1,
- f stands for 0 or 1,
- g stands for 0 or 1,
- h stands for 0 or 1,
- provided that at least one of e, f, g, and h is different from 0.

3. The process according to claim 1, wherein the agent (a) comprises at least one organic silicon compound (a1) of formula (I), $R_1R_2N$-L-Si(OR$_3$)$_a$(R$_4$)$_b$ (I), where
- $R_1$, $R_2$ both represent a hydrogen atom, and
- L represents a linear, divalent $C_1$-$C_6$-alkylene group,
- $R_3$, $R_4$ independently represent a methyl group or an ethyl group,
- a stands for the number 3 and
- b stands for the number 0.

4. The process according to claim 2, wherein the agent (a) comprises at least one organic silicon compound (a1) of formula (I) selected from the group of
- (3-Aminopropyl)triethoxysilane,
- (3-Aminopropyl)trimethoxysilane,
- -1-(3-Aminopropyl)silantriol,
- (2-Aminoethyl)triethoxysilane,
- (2-Aminoethyl)trimethoxysilane,
- -1-(2-Aminoethyl)silantriol,
- (3-Dimethylaminopropyl)triethoxysilane,
- (3-Dimethylaminopropyl)trimethoxysilane,
- -1-(3-Dimethylaminopropyl)silantriol,
- (2-Dimethylaminoethyl)triethoxysilane,
- (2-dimethylaminoethyl)trimethoxysilane, and/or
- 1-(2-Dimethylaminoethyl)silantriol.

5. The process according to claim 1, wherein the agent (a) comprises at least one organic silicon compound (a1) of formula (II), $(R_5O)_c(R_6)_d$ Si-(A)$_e$-[NR$_7$-(A')]$_f$-[O-(A")]$_g$-[NR$_8$- (A''')]$_h$-Si(R$_6$')$_d$(OR$_5$')$_{c'}$ (II), where
- e and f both stand for the number 1,
- g and h both stand for the number 0,
- A and A' independently represent a linear, divalent $C_1$-$C_6$ alkylene and
- R7 represents a hydrogen atom, a methyl group, a 2-hydroxyethyl group, a 2-alkenyl group, a 2-aminoethyl group or a group of formula (III)

-(A"")-Si(R$_6$")$_d$"(OR$_5$")$_{c''}$ (III),

- c stands for an integer from 1 to 3,
- d stands for the integer 3-c,
- c" stands 'for an integer from 1 to 3,
- d' stands for the integer 3-c',
- c" stands, for an integer from 1 to 3,
- d" stands for the integer 3-c",
- e stands for 0 or 1,
- f stands for 0 or 1,
- g stands for 0 or 1,
- h stands for 0 or 1,
- provided that at least one of e, f, g, and h is different from 0.

6. The process according to claim 2, wherein the agent (a) comprises at least one organic silicon compound (a1) of formula (II) selected from the group of
- 3-(Trimethoxysilyl)-N43-(trimethoxysilyl)propyl]-1-propanamine,
- 3-(Triethoxysilyl)-N-[3-(triethoxysilyl) propyl]-1-propanamine,
- N-Methyl-3-(trimethoxysilyl)-N43-(trimethoxysilyl)propyl]-1-propanamine,
- N-Methyl-3-(triethoxysilyl)-N43-(triethoxysilyl)propyl]-1-propane amine,
- 2-[Bis[3-(trimethoxysilyl) propyl]amino]-ethanol,
- 2-[Bis[3-(triethoxysilyl) propyl]amino]-ethanol,
- 3-(Trimethoxysilyl)-N,N-bis[3-(trimethoxysilyl) propyl]-1-propanamine,
- 3-(Triethoxysilyl)-N,N-bis[3-(triethoxysilyl) propyl]-1-propanamine,
- N1,N1-bis [3-(trimethoxysilyl)propyl]-1,2-ethanediamine,
- N1,N1-bis [3-(triethoxysilyl)propyl]-1,2-ethanediamine,
- N,N-bis[3-(trimethoxysilyl)propyl]-2-propen-1-amine, and/or
- N,N-bis[3-(triethoxysilyl)propyl]-2-propen-1-amine.

7. The process according to claim 1, wherein the agent (a) comprises at least one organic silicon compound (a1) of formula (IV), $R_9Si(OR_{10})_k(R_{11})_m$ (IV), where
- R9 stands for a $C_1$-$C_{18}$ is alkyl group,
- $R_{10}$ represents a hydrogen atom or a $C_1$-$C_6$ alkyl group,
- $R_{11}$ represents a $C_1$-$C_6$ alkyl group,
- k is an integer from 1 to 3, and
- m stands for the integer 3-k.

8. The process according to claim 7, wherein the agent (a) comprises at least one organic silicon compound (a1) of formula (IV) selected from the group of:
- Methyltrimethoxysilane,
- Methyltriethoxysilane,
- Ethyltrimethoxysilane,
- Ethyltriethoxysilane,
- Hexyltrimethoxysilane,
- Hexyltriethoxysilane,
- Octyltrimethoxysilane,
- Octyltriethoxysilane, Dodecyltrimethoxysilane,
Dodecyltriethoxysilane,
Octadecyltrimethoxysilane,
Octadecyltriethoxysilane, and
Mixtures of these.

9. The process according to claim 1, wherein the agent (a) comprises at least two structurally different organic silicon compounds (a1).

10. The process according to claim 1, wherein the substrate platelet comprises a material selected from the group of metals, metal alloys and metal oxides.

11. The process of claim 1, wherein the substrate platelet comprises aluminum.

12. The process according to claim 1, wherein the substrate platelet comprises a coating A of at least one low refractive index metal oxide and/or metal oxide hydrate having a refractive index of at most about 1.8.

13. The process according to claim 1, wherein the substrate platelet comprises a coating B of at least one highly refractive metal oxide having a refractive index of at least about 1.9.

14. The process according to 13, wherein the substrate platelet has a further coating C of at least one metal oxide and/or metal oxide hydrate which is different from the underlying coating B.

15. A kit-of-parts for dyeing keratinous material, comprising separately packaged
a first container comprising an agent (a'), wherein the agent (a') comprises:
(a1) at least one organic silicon compound selected from the group of silanes having one, two or three silicon atoms, and
a second container comprising an agent (a"), the agent (a") comprising:
(a2) at least one colorant compound comprising at least one substrate platelet-based pigment comprising a vacuum metallized pigment,
a third container containing an agent (b), wherein the agent (b) comprises:
(b1) at least one sealing reagent.

16. The process according to claim 3, wherein L represents a propylene group (—CH$_2$—CH$_2$—CH$_2$—) or an ethylene group (—CH$_2$—CH$_2$—).

17. The process according to claim 1, wherein the agent (a) comprises at least one organic silicon compound (a1) of formula (I),

where
R$_1$, R$_2$ both represent a hydrogen atom, and
L represents a linear, divalent C$_1$-C$_6$-alkylene group,
R$_3$, R$_4$ independently represent a methyl group or an ethyl group,
a stands for the number 3 and
b stands for the number 0, and at least one organic silicone compound (a1) of formula (IV),

where
R$_9$ stands for a C$_1$-C$_{18}$ alkyl group,
R$_{10}$ represents a hydrogen atom or a C$_1$-C$_6$ alkyl group,
R$_{11}$ represents a C$_1$-C$_6$ alkyl group,
k is an integer from 1 to 3, and
m stands for the integer 3-k.

18. The process according to claim 1, wherein the at least one at least one sealing reagent (b1) comprises a compound selected from the group of film-forming polymers, alkalizing agents, acidifying agents, and mixtures thereof.

19. The process according to claim 18, wherein the at least one at least one sealing reagent (b1) comprises a film-forming polymer.

20. The process according to claim 19, wherein the at least one at least one sealing reagent (b1) comprises an ethylene/sodium acrylate copolymer.

* * * * *

UNITED STATES PATENT AND TRADEMARK OFFICE
CERTIFICATE OF CORRECTION

| | | |
|---|---|---|
| PATENT NO. | : 11,992,546 B2 | |
| APPLICATION NO. | : 17/441265 | |
| DATED | : May 28, 2024 | |
| INVENTOR(S) | : Torsten Lechner et al. | |

It is certified that error appears in the above-identified patent and that said Letters Patent is hereby corrected as shown below:

In the Claims

Column 66, Line 26 change "3-(Trimethoxysilyl)-N43-(trimethoxysilyl)propyl]-1-propanamine" to
-- 3-(Trimethoxysilyl)-N[3-(trimethoxysilyl)propyl]-1-propanamine --.

Column 66, Line 30 change "N-Methyl-3-(trimethoxysilyl)-N43-(trimethoxysilyl)propyl]-1-propanamine" to -- N-Methyl-3-(trimethoxysilyl)-N[3-(trimethoxysilyl)propyl]-1-propanamine --.

Column 66, Line 32 change "N-Methyl-3-(triethoxysilyl)-N43-(triethoxysilyl)propyl]-1-propan amine" to -- N-Methyl-3-(triethoxysilyl)-N[3-(triethoxysilyl)propyl]-1-propanamine --.

Signed and Sealed this
First Day of October, 2024

Katherine Kelly Vidal
*Director of the United States Patent and Trademark Office*